(12) United States Patent
Ara et al.

(10) Patent No.: US 9,486,161 B2
(45) Date of Patent: Nov. 8, 2016

(54) INFORMATION PROCESSING SYSTEM AND METHOD

(75) Inventors: Koji Ara, Tokyo (JP); Tomoaki Akitomi, Tokyo (JP); Kazuo Yano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 506 days.

(21) Appl. No.: 14/124,067

(22) PCT Filed: Jun. 7, 2011

(86) PCT No.: PCT/JP2011/063003
§ 371 (c)(1),
(2), (4) Date: Mar. 6, 2014

(87) PCT Pub. No.: WO2012/169003
PCT Pub. Date: Dec. 13, 2012

(65) Prior Publication Data
US 2014/0379292 A1    Dec. 25, 2014

(51) Int. Cl.
*G01P 15/00*   (2006.01)
*G01P 11/00*   (2006.01)
*A61B 5/11*    (2006.01)
*G06F 19/00*   (2011.01)

(52) U.S. Cl.
CPC ............... *A61B 5/11* (2013.01); *A61B 5/1123* (2013.01); *G01P 15/00* (2013.01); *G06F 19/3481* (2013.01)

(58) Field of Classification Search
CPC ..... G01P 15/00; G06F 19/3481; A61B 5/11; A61B 5/1123; A61B 5/1038; A61B 5/112
USPC .................................. 702/127, 141, 142, 149
See application file for complete search history.

(56) References Cited

U.S. PATENT DOCUMENTS

| | | | | |
|---|---|---|---|---|
| 7,387,611 B2 * | 6/2008 | Inoue | ................... | A61B 5/1038 600/585 |
| 7,451,056 B2 * | 11/2008 | Flentov | ................ | A42B 3/0433 342/104 |
| 8,949,070 B1 * | 2/2015 | Kahn | ................... | G01C 22/006 702/141 |

OTHER PUBLICATIONS

Nakamura, Toru, et al.; Universal Scaling Law in Human Behavioral Organization; Sep. 28, 2007; pp. 1-4; Physical Review Letters, week ending Sep. 28, 2007; The American Physical Society.
Tanaka, Takeshi; Life Microscope: Continuous Daily-Activity Recording System with Tiny Wireless Sensor; 4 pages.

* cited by examiner

*Primary Examiner* — An Do
(74) *Attorney, Agent, or Firm* — Foley & Lardner LLP

(57) ABSTRACT

An information processing system includes a sensor node and a server. The sensor node obtains acceleration data and transmits the data to the server. The server obtains and records the number of zero crossings from the acceleration data. The server obtains and records the frequency distribution of the number of zero crossings. The server obtains one or more of the following: the slope of the approximate line of the distribution; the linearity of the distribution; the inflection point; the slope of the approximate line in the zero crossing range below the inflection point; the slope of the approximate line in the zero crossing range above the inflection point; the linearity of the distribution in the zero crossing range below the inflection point; and the linearity of the distribution in the zero crossing range above the inflection point. Then, the server records the obtained value.

17 Claims, 26 Drawing Sheets

FIG. 3

TEAMINFO

| USER ID | UNAME | GROUP ID | GLEADER | TEAM ID | TLEADER | POS ID | ROOM ID | FLOOR ID | BLD ID |
|---|---|---|---|---|---|---|---|---|---|
| 1 | W1 | A | 1 | A | 0 | 1 | RM1 | FL11 | BLD1 |
| 2 | W2 | A | 0 | A1 | 1 | 2 | RM1 | FL11 | BLD1 |
| 3 | W3 | A | 0 | A1 | 0 | 3 | RM1 | FL11 | BLD1 |
| 4 | W4 | A | 0 | A1 | 0 | 3 | RM2 | FL11 | BLD1 |
| 5 | W5 | A | 0 | A2 | 1 | 2 | RM3 | FL11 | BLD1 |
| 6 | W6 | A | 0 | A2 | 0 | 3 | RM4 | FL12 | BLD1 |
| 7 | W7 | A | 0 | A2 | 0 | 3 | RM4 | FL12 | BLD1 |
| 8 | W8 | B | 1 | B | 0 | 1 | RM4 | FL12 | BLD1 |
| 9 | W9 | B | 0 | B1 | 1 | 2 | RM5 | FL13 | BLD1 |
| 10 | W10 | B | 0 | B1 | 0 | 3 | RM6 | FL14 | BLD1 |
| 11 | W11 | B | 0 | B2 | 1 | 2 | RM7 | FL14 | BLD1 |
| 12 | W12 | B | 0 | B2 | 0 | 3 | RM8 | FL21 | BLD2 |
| 13 | W13 | C | 1 | C | 0 | 1 | RM9 | FL31 | BLD3 |
| 14 | W14 | C | 0 | C1 | 1 | 2 | RM9 | FL31 | BLD3 |
| 15 | W15 | C | 0 | C1 | 0 | 3 | RM9 | FL31 | BLD3 |
| 16 | W16 | D | 1 | D | 0 | 1 | RM10 | FL41 | BLD4 |
| 17 | W17 | D | 0 | D1 | 1 | 2 | RM11 | FL41 | BLD4 |
| 18 | W18 | D | 0 | D1 | 0 | 3 | RM12 | FL41 | BLD4 |

FIG.4

AEDATA

| RUSID | RSMIN | ATEMP | ALUX | AHUM | ZC | ACTV | COMM | LOC |
|---|---|---|---|---|---|---|---|---|
| 1 | 0:00 | 26.3 | 400.1 | 40.2 | 2.4 | 1 | 0 | POS1 |
| 1 | 0:01 | 26.4 | 400.2 | 40.2 | 0.3 | 0 | 1 | POS2 |
| 1 | 0:02 | 26.4 | 399.9 | 40.3 | 2.1 | 1 | 1 | POS2 |
| 2 | 0:00 | 25.1 | 400.8 | 42.2 | 1.7 | 0 | 0 | POS1 |
| 2 | 0:01 | 25.2 | 400.7 | 42.3 | 1.8 | 0 | 0 | POS2 |
| 2 | 0:02 | 25.1 | 398.1 | 42.2 | 1.9 | 0 | 0 | POS2 |

FIG.5

ACTIVITY LIST

| TIME | ACTIVITY DETERMINATION |
|---|---|
| 10:00:00 | 0 |
| 10:00:01 | 1 |
| 10:00:02 | 0 |

INFORMATION PROCESSING SYSTEM AND METHOD

BACKGROUND

The present invention relates to an information processing system and method, and more particularly to an information processing system and method for collecting, counting, and displaying human movement by using a sensor device.

Along with the development of the technology, sensing devices for constantly monitoring human behavior have been developed. These devices include sensors, such as acceleration, temperature, voice, and location information sensors, within a device that a person can wear and carry, such as a wristwatch, name tag, or mobile phone. For example, a sensor described in Non-patent document 1 (Tanaka, "Life Microscope: Continuous daily-activity recording system with tiny wireless sensor", International Conference on Networked Sensing Systems, Jun. 17, 2008, pp. 162-165) aims at managing health care, such as recovery from fatigue and dieting, and health promotion by measuring the amount of daily human activity, the number of steps, and the like.

Zero-crossing frequency is an index used for the amount of activity. This is the index for indicating how many hertz (Hz) at which a wearer performs the action from the information obtained by an accelerator. For example, typically a frequency of about 2 Hz is shown in walking and a frequency of about 0.5 Hz is shown even in a resting state such as web browsing. It can be arithmetically obtained by calculating the square root of the sum of the squared values of each of the x, y, and z axes measured by the accelerator. The index can be calculated per unit time, for example, every one minute, and used as an indication of the amount of activity in that one minute. This definition is used as an example of the amount of activity in the following description of the present specification. However, it is also possible to use an index showing the magnitude of the action, such as the absolute value of acceleration or the number of steps, which is correlated with the above definition to some extent.

SUMMARY

With the development of low power devices, it is possible to measure data constantly for 24 hours. However, this leads to some problems. One is the problem of the amount of data. When sensing information is obtained at a certain frequency for 24 hours, it is necessary to have enough storage capacity to store the data. For example, only if the three-axis acceleration is simply obtained at 50 Hz, it is necessary to have a storage capacity of approximately 20 megabytes per day. Several times this capacity is required in order to obtain a plurality of types of data for several days. It is necessary to reduce the amount of data to be stored in order to obtain information for a long time as possible. Further, the data obtained by the sensing device are collected in a data server by wireless or wired communication. Thus, if the amount of data per person can be reduced, it is possible to reduce the disk space required for the data server in which data of a plurality of persons are stored.

Further, the reduction in the amount of data allows not only effective use of a hard disk device, but also increasing the data transfer speed (or reducing the transfer time) between devices or data centers and a base station or relay station between them. Thus, low power consumption can be expected.

The second problem is related to a display on which the data user, such as the wearer, browses the obtained data. When data is obtained for a certain period of time, such as for 24 hours a day for one month, it is very difficult for the user to know significant features and tendencies from the obtained data if all data is provided as it is to the user. It is preferable to display data that clearly shows the features to the data user. In particular, there is a problem in data browsing using a small tiny device for browsing. For example, it is assumed that human behavior is obtained by a wristwatch-type sensing device and the result is displayed on the wristwatch. The wristwatch has a very small area to display information. It is necessary to display data in a display area of at most about 3 cm*3 cm. Naturally, it is necessary to narrow down the information to be displayed to make it easy to interpret the features of the data.

Conventionally, there are several methods for arithmetically reducing the features of a distribution. For example, average and standard deviation are used as basic indices. However, these indices have problems.

For example, with the average it is possible to know the average of the amount of activity in the entire period. In this case, however, it is difficult to know the distribution of the action in a time period. For example, if the amount of activity of a person who has stress and fatigue varies in a day, the variation of the amount of activity is not visible when the data is averaged. The standard deviation is the typical index to know the width of the distribution. When a certain event occurs, this index indicates how far the event expands from the average. This index has other problems. First, one problem is that the amount of human activity does not necessarily have a normal distribution as described below. Simply stated, the state of a low amount of activity is more than the state of a high amount of activity. Such a distribution is not well expressed by the standard deviation index. The second problem is that a characteristic phenomenon of low frequency is not visible.

One method for addressing the above problems is to store the frequency at which the amount of activity occurs in the range of a certain value, namely, the so-called histogram. For example, when the amount of activity can be distributed from 0 Hz to 5 Hz, the method defines the width at an interval of 0.5 Hz, and stores the range and the number of times the actual action occurs. For example, the method records the occurrence frequency for each width, such as, for example, 10 times at 0 or more and less than 0.5 Hz, 12 times at 0.5 Hz or more and less than 1 Hz, and three times at 1 Hz or more and less than 1.5 Hz. This is the same for other indices such as the number of steps. For example, in the case of the number of steps, it is possible to count the number of steps per unit time as the histogram.

The histogram has an advantage that the original state is likely to be reproduced as the width is made very small, regardless of the distribution in which the action occurs. However, the smaller the width the more the amount of data for storing the information increases. Simply stated, when the width is made small and the number of widths is 10 times the original number, the capacity required to store all the appearance frequencies should be 10 times.

In view of the foregoing, an object of the present invention is to compress the information related to the human behavior obtained by sensing into information with less amount of information showing the features of the human behavior. Further, another object of the present invention is to solve the problems such as the increase in the amount of data, the increase in the network load, and the display to a small device.

A summary of a typical one of the inventive aspects of the invention disclosed in this application will be briefly described as follows.

An information processing system includes, for example, a sensor, a base station, and a server. The sensor obtains acceleration data and transmits the data to the server through the base station. The server obtains and records the number of zero crossings from the acceleration data. The server obtains and records one or more of the following: the slope of the approximate line of the distribution, the linearity of the distribution, the inflection point, the slope of the approximate line in the zero crossing range below the inflection point, the slope of the approximate line in the zero crossing range above the inflection point, the linearity of the distribution in the zero crossing range below the inflection point, and the linearity of the distribution in the zero crossing range above the inflection point. Then, the server stores the obtained value in a display device connected to the information system.

Further, the information processing system includes a questionnaire interface for asking questions about human stress. The server calculates and records the weight of each feature so that the error between the feature and the questionnaire result is reduced. The server estimates and records stress from the weights of the individual features. Then, the server outputs the estimated value to a display device connected to the information system.

According to a first aspect of the present invention, there is provided an information processing system including: a sensor for measuring the human acceleration produced by human movement for a predetermined time period; a processing part for obtaining feature data related to the speed of human movement based on the measured acceleration data; and a storage part for storing the obtained feature data. The processing part includes: obtaining the speed of movement per predetermined unit time from the acceleration data measured by the sensor; counting the speed of movement above a reference value, from the obtained speed of movement per unit time with respect to each of a plurality of reference values of the speed of movement, as the cumulative frequency for the reference value of the speed of movement; and obtaining statistical data based on the distribution between the reference value of the speed of movement and the log of the cumulative frequency for the reference value, as the feature data of human behavior, and storing the obtained feature data in the storage part.

In the information processing system described above, for example, the speed of movement is the zero crossing number indicating the number of times the acceleration data is zero or crosses zero. The processing part obtains the number of zero crossings per predetermined unit time as the speed of movement, from the acceleration data measured by the sensor. Then, the processing part counts the number of zero crossings above a reference value, from the number of zero crossings obtained per unit time with respect to each of a plurality of reference values of the zero crossing number, as the cumulative frequency for the reference value of the zero crossing number. Then, the processing part obtains statistical data as the feature data of human behavior and stores the obtained feature data in the storage part.

In the information processing system described above, the processing part obtains an index indicating, for example, the slop or linearity of one approximate line or a plurality of approximate lines with respect to the distribution, as feature data.

In the information processing system described above, the processing part obtains feature data including, for example, one or more of the following first to fourth feature data. The first feature data is the inflection point at which the distribution between the reference value of the zero crossing number and the log of the cumulative frequency for the reference value, is approximated by a curve or a plurality of straight lines. The second feature data is the slope of a first approximate line in the zero crossing range below the inflection point. The third feature data is the slope of a second approximate line in the zero crossing range above the inflection point. The fourth feature data is the index indicating the linearity of the distribution in the zero crossing range below the inflection point. Then, the processing part stores the obtained feature data in the storage part.

In the information processing system, the feature data can includes all of the first to fourth feature data.

In the information processing system, the feature data can also include one or more of the following: the slope of the approximate line of the entire distribution, the linearity of the entire distribution, and the linearity of the distribution in the zero crossing range above the inflection point.

In the information processing system, the processing part may obtain feature data including one or more of the following: the average of the number of zero crossings; the slope of a third approximate line in the zero crossing range below the average of the number of zero crossings; the slope of a fourth approximate line in the zero crossing range above the average of the number of zero crossings; the difference between the slope of the third approximate line and the slope of the fourth approximate line; and the slope of the approximate line of the entire distribution. Then, the processing part may store the obtained feature data in the storage part.

In the information processing system, the processing part can output the obtained feature data to a display device.

The information processing system can be configured by including: a sensor node including the sensor and a transmission part for transmitting the measured acceleration data; and a server including a receiving part for receiving the acceleration data from the sensor node, the processing part, and the storage part.

Further, the information processing system may be configured by including a sensor node including the sensor, the processing part, and the storage part.

The information processing system includes a plurality of the above described sensors. The individual sensors can measure the acceleration of each person to be measured. The processing part can obtain the first to fourth feature data for each person to be measured, input the previously indexed stress value of the person to be measured, obtain each weight coefficient so that the sum of the error between the estimated stress value obtained based on the obtained first to fourth feature data and on the obtained weight coefficients of each of the first to fourth feature data, and the input stress value is reduced, with respect to each person to be measured, and store the obtained weight coefficients in the storage part.

In the information processing system, the processing part can obtain estimated stress value based on the obtained first to fourth feature data and on the weight coefficients for each of the first to fourth feature data. Then, the processing part can store the obtained estimated stress values in the storage part.

According to a second aspect of the present invention, there is provided an information processing system including: a sensor for measuring the human acceleration produced by human movement for a predetermined time period; a processing part for obtaining feature data related to the speed of human movement, based on the measured acceleration data; and a storage part for storing the obtained feature data. The processing part includes: obtaining the speed of movement per predetermined unit time from the acceleration data measured by the sensor; determining active or inactive state in a particular time based on whether the speed of movement per unit time exceeds a predetermined threshold; obtaining the duration of the active state and/or the duration of the inactive state in chronological order; counting the duration above a reference value, from the obtained duration of the active state and/or the obtained duration of the inactive state with respect to each of a plurality of reference values of the duration, as the cumulative frequency for the reference value of the duration; obtaining statistical data based on the reference value of the duration, and on the log of the cumulative frequency for the reference value, as the feature data of human behavior; and storing the obtained feature data in the storage part.

In the information processing system, the speed of movement is the zero crossing number that indicates, for example, the number of times the acceleration data is zero or crosses zero.

In the information processing system, the processing part obtains an index indicating, for example, the slop or linearity of one approximate line or a plurality of approximate lines with respect to the distribution, as feature data In the information processing system, the processing part obtains feature data including, for example, one or more of the following first to seventh feature data. The first feature data is the inflection point at which the distribution between the reference value of the duration and the log of the cumulative frequency for the reference value, is approximated by a curve or a plurality of straight lines. The second feature data is the slope of a first approximate line in the duration range below the inflection point. The third feature data is the slope of a second approximate line in the duration range above the inflection point. The fourth feature data is the index indicating the linearity of the distribution in the duration range below the inflection point. The fifth feature data is the average of the duration. The sixth feature data is the slope of a third approximate line in the duration range below the average of the duration. The seventh feature data is the slope of a fourth approximate line in the duration range above the average of the duration. Then, the processing part stores the obtained feature data in the storage part.

In the information processing system, the feature data can also include one or more indices, indicating the difference between the slope of the third approximate line and the slope of the fourth approximate line, and the linearity of the entire distribution.

According to a third aspect of the present invention, there is provided an information processing method. In the information processing method, a processing part obtains the speed of a movement per predetermined unit time, from the acceleration data measured by a sensor for measuring the human acceleration produced by human movement for a predetermined time period. Then, the processing part counts the speed of movement above a reference value, from the obtained speed of movement per unit time, with respect to each of a plurality of reference values of the speed of movement, as the cumulative frequency for the reference value of the speed of movement. Then, the processing part obtains statistical data based on the distribution between the reference value of the speed of movement and the log of the cumulative frequency for the reference value, as the feature data of human behavior. Then, the processing part stores the obtained feature data in a storage part.

According to a fourth aspect of the present invention, there is provided an information processing method. In the information processing method, a processing part obtains the speed of movement per predetermined unit time, from the acceleration data measured by a sensor for measuring the human acceleration produced by human movement for a predetermined time period. Then, the processing part determines active or inactive state in a certain time based on whether the speed of movement per unit time exceeds a predetermined threshold; obtaining the duration of the active state and/or the duration of the inactive time in chronological order. Then, the processing part counts the duration above a reference value, from the obtained duration of the active state and/or the obtained duration of the inactive state, with respect to each of a plurality of reference values of the duration, as the cumulative frequency for the reference value of the duration. Then, the processing part obtains statistical data based on the reference value of the duration, and on the log of the cumulative frequency for the reference value, as the feature data of human behavior. Then, the processing part stores the obtained feature data in a storage part.

According to the aspects of the present invention, it is possible to compress the information related to the human behavior obtained by sensing, into information with less amount of information showing the features of the human behavior. As a result, it is possible to solve the problems such as the increase in the amount of data, the increase in the network load, and the display to a small tiny device.

BRIEF DESCRIPTION OF THE DRAWINGS

FIG. 3 is an example of a personal information table according to the first embodiment;

FIG. 4 is an example of an activation list according to the first embodiment;

FIG. 5 is an example of a behavior analysis data table according to the first embodiment;

DETAILED DESCRIPTION

Figure 1:
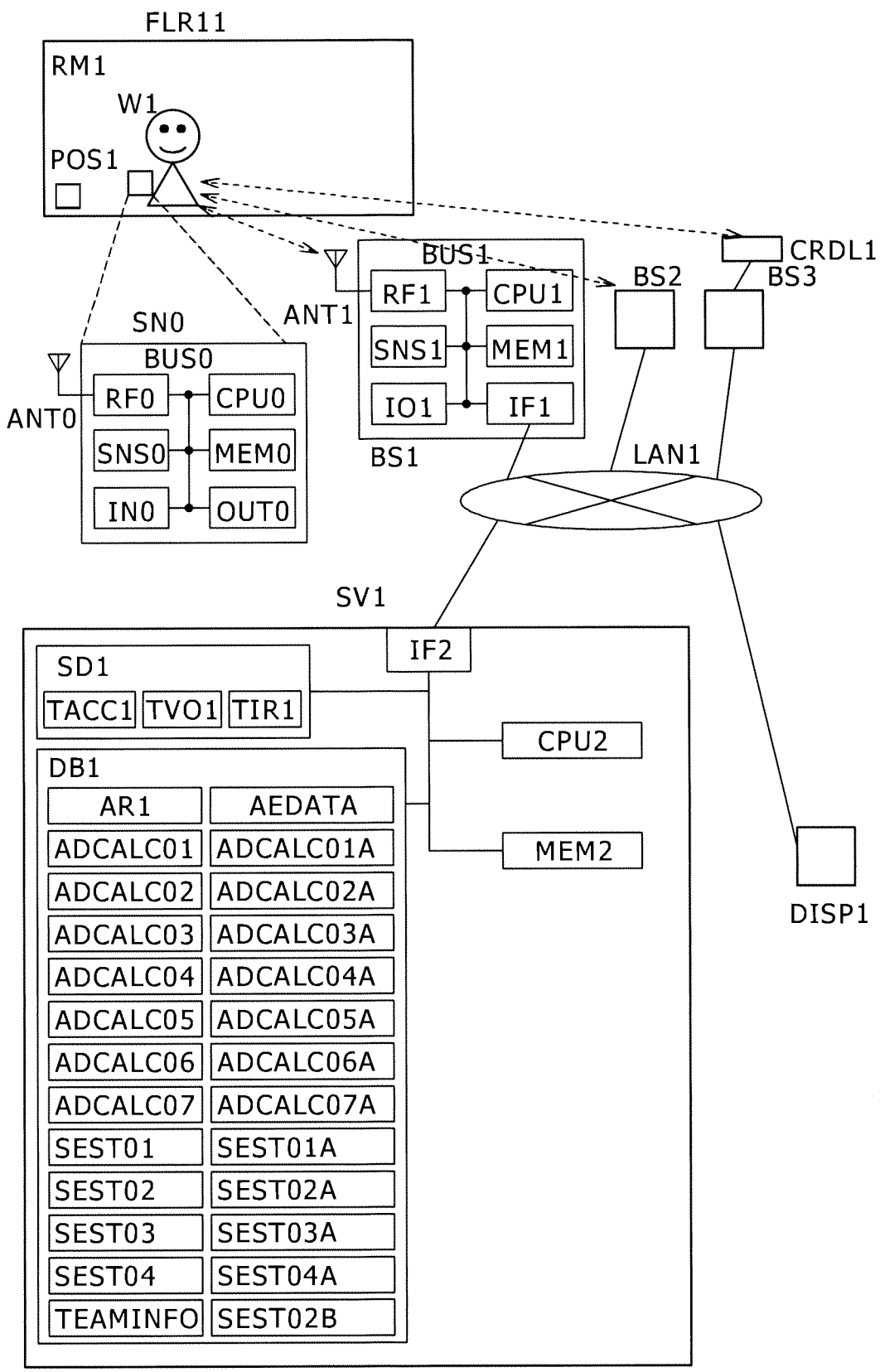
FIG. 1 is an example of the configuration of the entire system according to a first embodiment.

Hereinafter, embodiments of the present invention will be described in detail with reference to the accompanying drawings. Note that the same or similar components are designated by the same reference numerals throughout the figures.

1. First Embodiment

FIG. 1 shows a system configuration of a first embodiment.

An information processing system includes, for example, a sensor node SN0, a base station BS1, and a management server SV1. Further, the information processing system may also include a position identification device POS1, a display device DISP1, and a cradle CRDL1.

A worker (a user, a wearer of the sensor node) W1 holds the sensor node SN0 with different types of sensors. The worker may hold a plurality of sensor nodes. The sensor node SN0 includes: a radio circuit RF0 including a processor CPU0 and an antenna ANT0; a sensor SNS0 such as different types of sensors for measuring sound, acceleration, humidity, illuminance, infrared light, color, RFID and the like, as well as a motion sensor; a memory MEM0 for storing a sensing program and a data processing program; an input device IN0 such as a button; and an output device OUT0 such as LCD, LED, or a buzzer.

In the sensor node SN0, the processor CPU executes the sensing program to obtain sensing data from various sensors at a predetermined sampling interval (for example, 0.05 seconds, and the like). Then, the sensor node SN0 adds the identifier for identifying the sensor node, the timestamp, and the like, to the obtained sensing data, and transmits the data to the base station device.

The sensor node SN0 can be realized by different forms. In particular, it is known that in the case of the sensor node worn directly on the body, such as a bracelet-type sensor node, it is possible to know the number of pulses by projecting infrared light into the body and sensing the reflection. This takes advantage of the fact that the change in the blood flow can be estimated from the reflection because the blood absorbs the infrared light. Further, it is also known that in the case of the sensor node worn on the closes, such as a name-tag type sensor node, it is possible to detect face-to-face contact between persons wearing the name tag, by the functions provided in the name tag to project infrared light to the outside and receive infrared light from the outside. In other words, if the worker W1 and another worker W2 wear the name-tag type sensor node SN0 and face each other, the sensor nodes of the two workers exchange their identifiers through infrared communication. Note that the details of the control of the sensor node can be the same as those described in Non-patent document 1 and Non-patent document 2 (Nakamura, "Universal Scaling Law in Human Behavioral Organization", PHYSICAL REVIEW LETTERS, Sep. 28, 2007).

The information sensed by the sensor node SN0 is transmitted to the base station device BS1 through wireless communication directly or through a repeater. It is also possible to collect the information through wired communication by the cradle CRDL1 with a function as a charger for data collection, and to transmit the collected information to a base station BS3. The information received by the base station BS is stored in a sensor database SD1 of the management server SV1 through a wired network LAN1.

The base station device BS1 includes: a processor CPU1; a radio circuit RF1; a memory MEM1 for storing a data transmission/reception program and a sensor node management program; an input/output device IO0 such as LCD, LED, buzzer, display, mouse, and keyboard; and an input/output IF1 for communicating with an external network such as the Internet. Further, the base station device BS1 may also include a sensor SNS1 such as sensors for detecting sound, acceleration, humidity, illuminance, infrared light, and color, as well as a motion sensor and RFID. The configuration of the base stations BS2 and BS3 are the same as the configuration of the base station device BS1. However, the base station BS3 includes an interface with the cradle CRDL1, a communication circuit, and the like, instead of or in addition to the radio circuit RF1.

When the processor CPU1 executes the data transmission/reception program, the base station device BS1 receives sensing data from the sensor node SN0 through wireless or wired communication. Then, the base station device BS1 transmits the data with its identifier to the management server SV1 through the wired network LAN1.

The position identification device POS1 is the hardware for detecting that the worker is present in a particular space. For example, the position identification device POS1 is the device for emitting infrared light including its identifier at regular intervals. When the worker W1 wearing the name-tag type sensor node SN0 works in front of the position identification device POS1, the sensor node SN0 can detect the infrared light. The information is transmitted through wireless communication, so that the management server SV1 can know the work place of each worker by matching the received identifier to the information on the location of the position identification device. It is also possible to limit the range of the location of the worker by wireless transmission/reception and positioning technology, or to identify the location of the worker by an RFID reader instead of using infrared light.

Further, the display device DISP1 used by the data audience is connected to LAN1 through wired or wireless LAN.

The management server SV1 includes a network interface IF2, a processor (processing part) CPU2, a memory MEM2, a sensor database SD1, and a recording device (storage part) DB1. The network interface IF2 is the interface for connecting to the wired network LAN1. The sensor database SD1 is the device for storing the sensing data obtained by each of the different sensors. The recording device DB1 is the device for recording various programs and data tables, which will be described below. Examples of the sensor database SD1 and the recording device DB1 are, for example, a hard disk drive, a CD-ROM drive, and a flash memory. Note that the sensor database SD1 and the recording device DB1 may be configured to a single recording device.

The processor CPU2 realizes various functions by reading the various programs stored in the recording device DB1 to the memory MEM2 and executing the programs.

Figure 2:
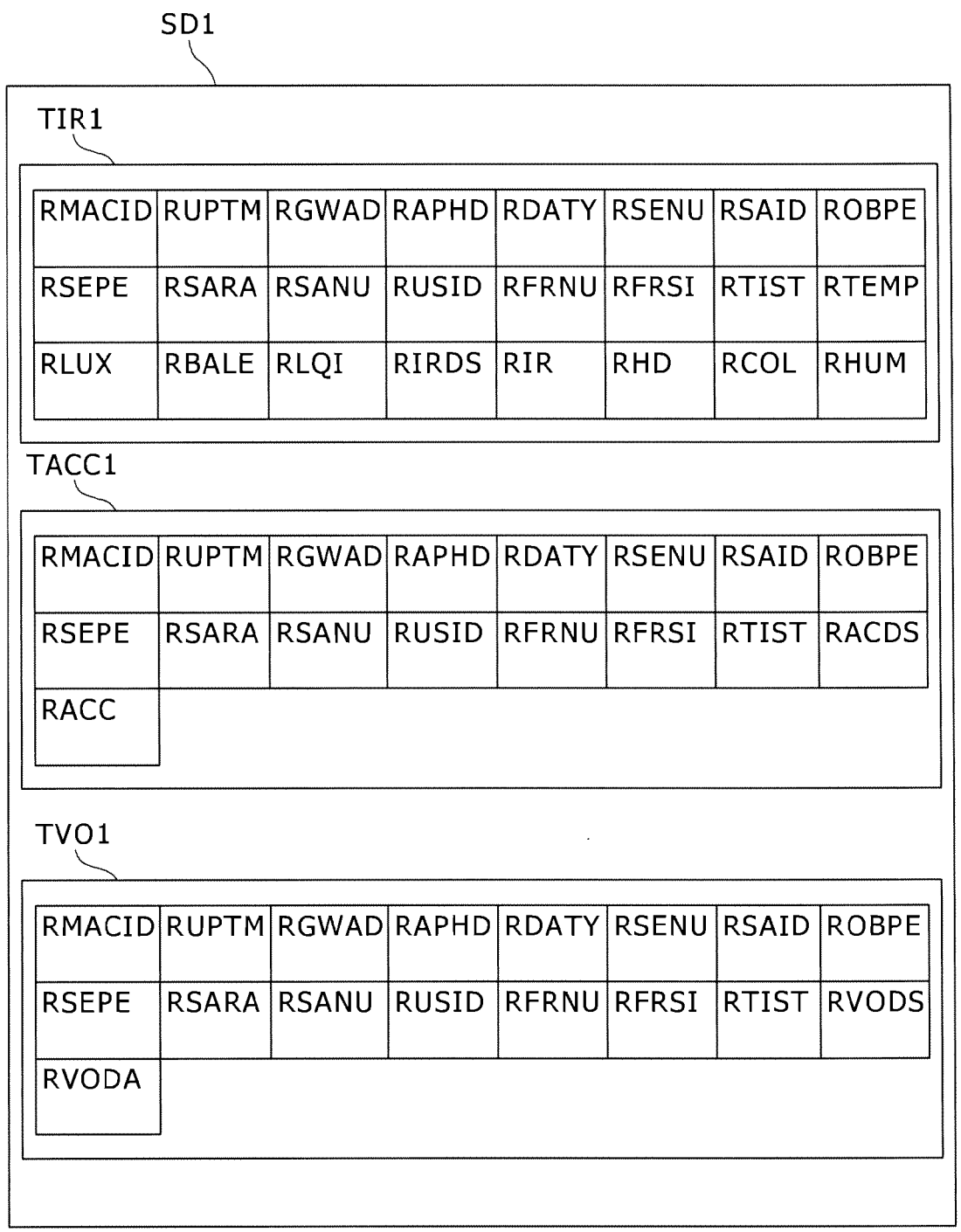
FIG. 2 is an example of the structure of a table for storing sensing data according to the first embodiment.

FIG. 2 is a view of an example of the sensing data that is transmitted by the sensor node SN0, received by the management server, and stored in the sensor data base SD1 of the management server SV1. The sensor data base SD1 manages the sensing data together with the identifier information of the sensor node used by the worker as well as the identifier information of the worker.

Table TIR1 is a table for storing temperature data, illuminance data, and infrared light detection data. Column RMACID stores the network address of the device. Column RUPTM registers the time when the data is stored in the table SD1. Column RGWAD stores the identifier of the base station device (for example, BS1) that received the data through wireless communication. Column RAPHD stores the type of the sensor node. For example, the number 1 is stored for the bracelet-type sensor node and the number 2 is stored for the name-tag type sensor node. Column RDATY stores the type of the data stored in a wireless packet. For example, the number 1 is stored for the infrared light detection data, the number 2 is stored for the acceleration data, and the number 3 is stored for the voice data. Column RSENU is a cyclic counter that gives the numbers from 0000 to FFFF to the frames by the sensor node in the transmission order, and then resets FFFF to 0000. When the divided frames are joined together, the sequence number of the first frame is stored. In column RSAID, the same sampling identifier is given to the divided frames including data sampled at the same sensing cycle. Column ROBPE stores the current sensing interval (for example, 10 sec/cycle). Column RSEPE stores the current wireless transmission interval of the sensor node. The number representing the interval or the value representing how much times the sensing interval can be stored in this column. Column RSARA stores the obtained cycle (for example, 50 Hz) of the sensor data in the sensor node. Column RSANU stores the current number of times of sampling in the sensor node.

Column RUSID stores the identifier ID of the user using the particular node. In column RFRNU, when the frame of data transmitted by the sensor node is divided into a plurality of frames, and for example, there are n divided frames in total, n, n−1, n−2, . . . , 3, 2, 1 are given in descending order. It is assumed that 1 represents the last divided frame and 0 represents the 256-th frame. Column RFRSI stores the total number of a series of frames to be transmitted separately. Column RTIST stores the time when the sensor node obtained the particular data by the sensor. Column RTEMP stores the temperature data obtained by the sensor node. Column RLUX stores the illuminance data obtained by the sensor node. Column RBALE stores the value showing the remaining capacity of the battery of the sensor node, for example, the power supply voltage. Column RLQI stores the value showing the wireless communication quality between the sensor node and the base station, for example, LQI (Link Quality Indicator). Column RIRDS stores the number of detected infrared data to be stored in the particular data. Column RIR stores the infrared data obtained by the sensor node. In this column, the identification ID of the other worker as well as the identification ID of the position identification device is stored as infrared data. Column RHD stores the data obtained by the motion sensor of the sensor node. Column RCOL stores the information obtained by the color sensor of the sensor node. Column RHUM stores the information obtained by the humidity sensor of the sensor node.

Table TACC1 stores the data of the acceleration sensor, instead of the data such as infrared light in the table TIR. From the column RMACID to the column RTIST, the same contents as those of the table TIR1 are stored. Column RACDS stores the number of detected acceleration data to be stored in the particular data. Column RACC stores the acceleration data obtained by the sensor node.

Table TVO1 stores the voice data instead of the data such as the infrared data in the table TIR. From the column RMACID to the column RTIST, the same contents as those of the table TIR1 are stored. Column RVODS stores the number of detected voice data to be stored in the particular data. Column RVODA stores the voice data obtained by the sensor node.

Note that each of the tables in the present embodiment is not limited to the form of the table and may be a storage area of an appropriate form.

FIG. 3 is a personal information table TEAMINFO stored in the recording device DB1 shown in FIG. 1. The personal information table TEAMINFO stores worker information such as the affiliation, job title, and department of each worker, in association with the identification ID of the worker. The worker information is input in advance by the data audience or other person by using an appropriate input part, referring to the input instruction, input area, and the like, displayed in the display device DISP1. Then, the worker information is stored in the personal information table TEAMINFO. For example, the following data are stored. Column USERID stores the identification ID of the worker using the sensor node. Column UNAME stores the name of the worker. Column GROUPID stores the ID for identifying the group to which the worker belongs. In this example, one team or a plurality of teams are present in a group. Column GLEADER stores the flag showing the leader of the group. For example, the number is stored for the leader of the group and the number 0 is stored for the other members. Column POSID stores the information showing the job title. For example, the number 1 is stored for the manager, the number 2 is stored for the assistant manager, and the number 3 is stored for the new employee. Column ROOMID stores the identification information of the room (office, and the like), which is formally registered as the location of each employee. Column FLOORID stores the information for identifying the floor where the room specified in the column ROOMID is present. Column BLDID stores the information for identifying the building and area where the floor specified in the column FLOORID is present.

FIG. 4 is an example of the structure of a behavior analysis data table AEDATA stored in the recording device DB1 of the management server SV1. The management server SV1 executes a behavior analysis program AR1 for the sensing data at a predetermined timing. Then, the management server SV1 interprets the behavior of each worker, and stores the data in the behavior analysis data table AEDATA.

The structure of the behavior analysis data table AEDATA shown in FIG. 5 will be described. Column RUSID stores the ID for identifying the worker. This can be obtained by referring to the value of RUSID in each of the tables shown in FIG. 2. Column RSMIN stores the time when the sensor node measured the data to be stored in the corresponding row. Here, it is assumed that each row stores data for one minute.

The program AR1 calculates the zero crossing number and the amount of activity of the worker, from the values of the number of detected acceleration data RACDS and the acceleration data RACC in the table TACC1 in which the acceleration information is stored, by the following method. Then, the obtained data are stored in a column ZC and a column ACTV.

Here, a method for determining whether each worker is in the active state or not will be described. Positive action in the operation allows the worker to develop ideas through the collection of information from inside and outside the company and through heated discussions. In this case, possible actions are "face-to-face contact including not only words but also gestures", "going to the other person's place to meet face-to-face with that person", and the like. The present inventors conducted experiments on the relationship between such user actions and the movement rhythm, and found that the frequency of the acceleration during the time period of an active operation is higher than the frequency of the acceleration during other time periods, from the video observation and the like. For example, during conversation, the frequency component from 2 to 3 Hz is increased. Thus, in this embodiment, the period in which the acceleration frequency exceeds a predetermined threshold is defined as the active state. Typically, the acceleration frequency is 2 Hz or more, and the like. Of course, the value differs depending on the individual and the type of operation, so that the setting can be changed according to the situation. It is possible to set a threshold by measuring the actual data, counting the distribution of the movement rhythm of each user, and obtaining, for example, the average or the upper 25% value.

Figure 6:
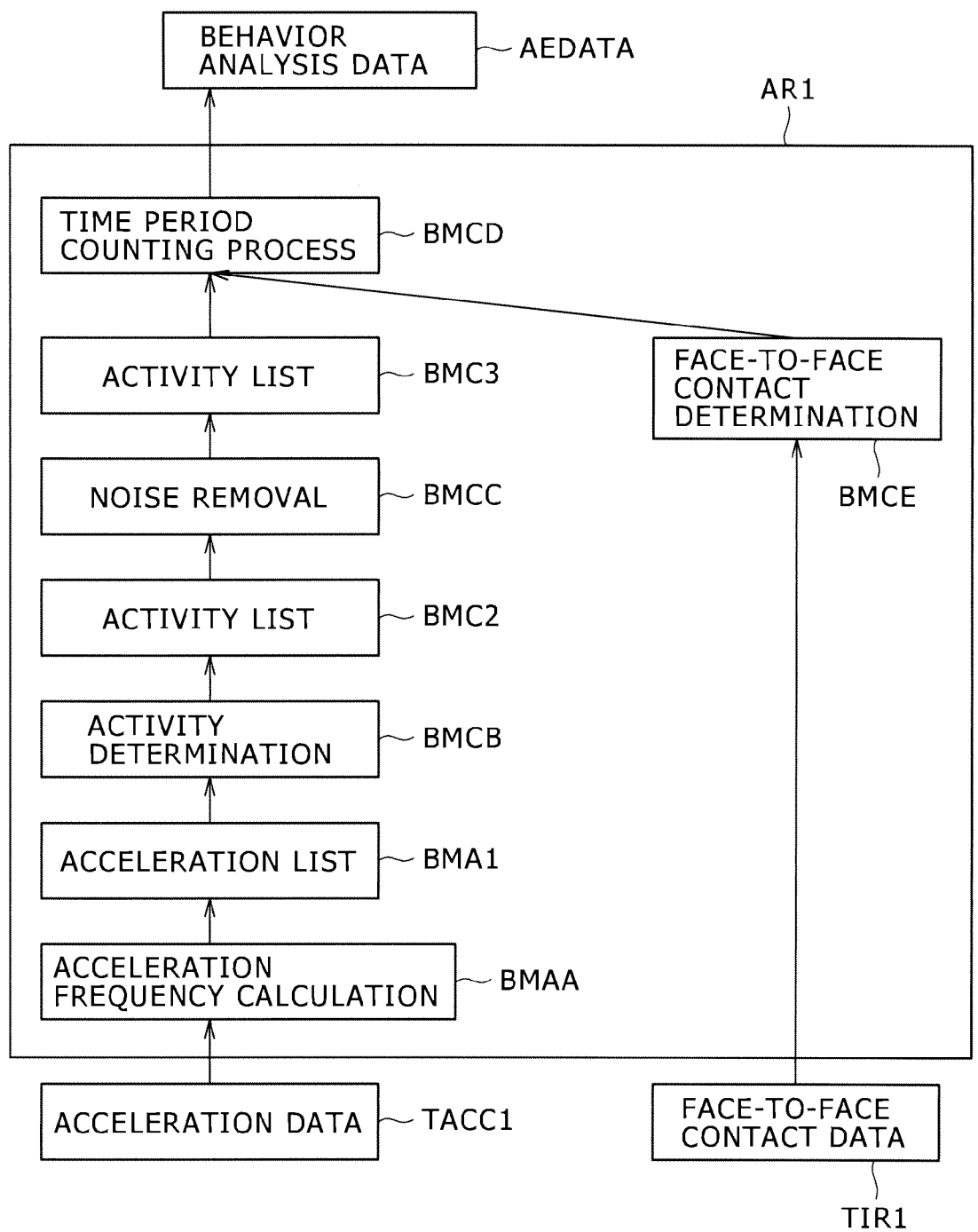
FIG. 6 is an example of the flow for calculating the amount of activity of a worker according to the first embodiment.

Calculation process AR1 of the activity level will be described with reference to FIGS. 5 and 6. The processes shown in FIGS. 5, 6, as well as the processes in other flow charts in the present specification are executed by the CPU2. The first acceleration frequency calculation (BMAA) is the process for obtaining a frequency from the acceleration data (TACC1) stored in chronological order. The frequency is defined as the number of oscillations of the wave per second. In other words, the frequency is the index indicating the intensity of the oscillation. The frequency may be calculated by Fourier transform. However, in the present embodiment, the zero crossing number (zero crossing frequency) regarded as corresponding to the frequency is used to simplify the calculation. Thus, the process load of the server is reduced. It is effective to solve the problem of the increase in the calculation amount in the server due to the increase in the number of sensor nodes. Note that other indicators related to the speed of human movement can also be used accordingly, in addition to the zero crossing number.

The zero crossing number is the number of times the value of the chronological data in a certain time period (or in a unit time) is zero. More precisely, the zero crossing number is the count of the number of times the chronological data changes from a positive value to a negative value or from a negative value to a positive value. For example, it is assumed that the period in which the acceleration value changes from positive to negative and changes again from positive to negative, is one cycle. In this case, it is possible to calculate the number of oscillations per second from the counted number of zero crossings. The number of oscillations per second, calculated as described above, can be used as the approximate frequency of the acceleration.

Further, the sensor node SN0 according to the present embodiment includes a three-axis acceleration sensor. Thus, it is possible to calculate one zero crossing number by summing zero crossing numbers in the three axis directions in the same time period. In particular, it is possible to detect minute pendulum motion in the left and right and forth and back directions, which can be used as an index indicating the intensity of the oscillation.

A value greater than the interval of a series of data, namely, the original sensing interval is set as "a certain time period" in order to count the number of zero crossings. For example, the number of zero crossings per second or per minute is obtained.

As a result of the acceleration frequency calculation (BMAA), the zero crossing number in each time, as well as the frequency per second calculated from the zero crossing number are generated as an acceleration list (BMA1) on the memory or as a file. Then, the generated value is stored in the column ZC of AEDATA.

Next, an activation determination (BMCB) is performed for the list (BMA1). As described above, it is determined whether active or inactive based on whether the acceleration exceeds a certain threshold. The list (BMA1) is scanned sequentially. For example, if the frequency (which can be obtained from the zero crossing number as described above) exceeds the threshold, the determination value "1" is inserted into the corresponding row as active state. If the frequency is below the threshold, the determination value "0" is inserted into the corresponding row as inactive state. As a result, an activation list (BMC2) is generated by determining whether active or inactive in each time period per second.

Here, it could be that even if the acceleration frequency is less than the threshold at a certain moment, the frequency exceeds the threshold and the active state is shown before and after that time, or even if the frequency exceeds the threshold at a certain moment, the frequency is less than the threshold and the inactive state is shown before and after that time. There may be a case for requiring a mechanism to remove such an instantaneous noise.

Thus, a noise removal (BMCC) is performed for the list (BMC2). The role of the noise removal is to generate, for example, a line "00000000111111111111", by removing the instantaneous change while adding the context to the chronological change in the amount of activity obtained as described above, such as, for example, a line "00010001111111001111". By performing such a noise removal process, the amount of activity can be calculated by taking into account the before and after the time period. As a result, it is possible to know the amount of activity reflecting the actual situation more accurately. The process for removing noise can be achieved by removing a high frequency component by a low pass filter. However, it is also possible to use a method like majority voting. Here, this will be described as a more simple method. In this method, each time period from the first to the last is to be determined, one by one, in chronological order. It is assumed that currently the ith time period is to be determined. Here, the numbers of time periods in the active state and the inactive state are calculated for 2n+1 time periods in total from the i−nth time period to the i+nth time period. Here, if the number of active time periods is greater and the i-th time period is in the inactive state, the i-th state is changed to the active state. On the other hand, if the number of inactive time periods is greater than the other, the i-th state is changed to the inactive state. For example, when this method is applied to the line "0001000111111001111" with n=2, the line "0000000111111111111" is generated. If n is small, noise reflecting only short time before and after is removed. If n is large, noise reflecting longer time is removed. The size of n depends on the person or the type of operation. For example, it is possible to remove noise in such a way that a short noise is first removed by a small n and a longer noise is removed again by a large n. With the method like majority voting as described above, it is possible to reduce the calculation amount of the server and reduce the process load. As a result, an activity list (BMC3) is generated by determining active or inactive in each time period (FIG. 5).

The activity list (BMC3) is the data per second. However, for the purpose of simplifying the later processing, the amount of activity can be calculated with a longer time unit by a time period counting process BMCD. Here is an example of calculating the amount of activity per minute from the amount of activity per second. One method is to count the number of seconds in active state for one minute, and if the number is greater than the threshold, consider the one-minute time period as the active state. For example, if the number of seconds exceeds 50%, the method considers it as the active state. The amount of activity of each worker calculated as described above is stored in the column ACTV. Then, the number "1" is stored for the active state, namely, if the behavior is active, while "0" is stored if the behavior is inactive.

Next, in a face-to-face contact determination process BMCE, the method determines whether the worker meets face-to-face with the other person at a particular time, and stores the data in the column COMM. For example, the number "1" is stored for face-to-face contact, while "0" is stored for not meeting face-to-face. The information can be obtained by referring to a column RIR of the table TIR1 of the sensor database SD1, to check whether the identification ID of the other worker is detected. The method counts the number of seconds in the face-to-face contact state during that one-minute time period. If the number is greater than the threshold, the method considers that the one-minute time period is in the face-to-face contact state. For example, the method considers it as the face-to-face contact state if the number exceeds 50%.

Figure 7:
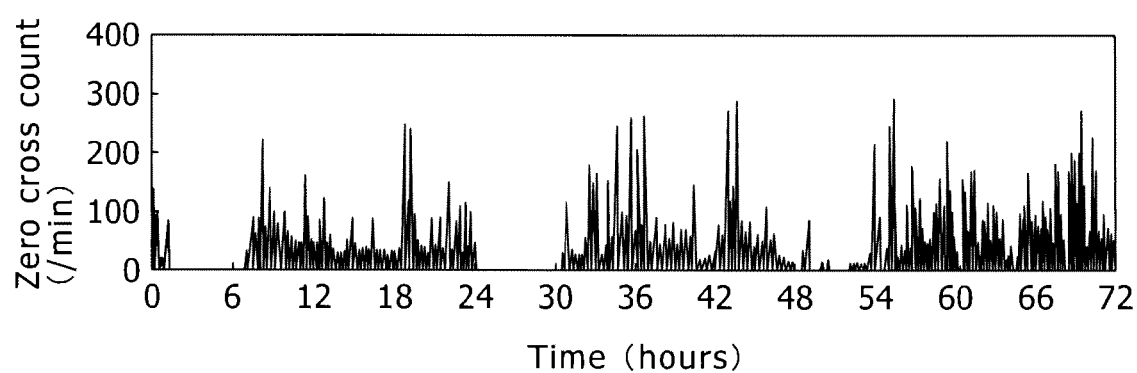
FIG. 7 is an example of the number of zero crossings of a worker according to the first embodiment.

The present inventors have focused on the frequency distribution of the number of zero crossings stored in BMA1 as described above. In other words, the point is that when plural zero crossings are obtained by a continuous measurement, what zero crossings are and how many times the zero crossings occur and that any distinct trend is present. If there is a feature common to different individuals with respect to the distribution of the zero crossings, the feature can be indexed to show the feature of their behavior with a small amount of data. FIG. 7 and subsequent figures show the features of human behavior that can be seen from the actual data.

FIG. 7 is a graph of the change in the number of zero crossings per minute obtained from a wristwatch-type sensor for three days (72 hours).

Figure 8:
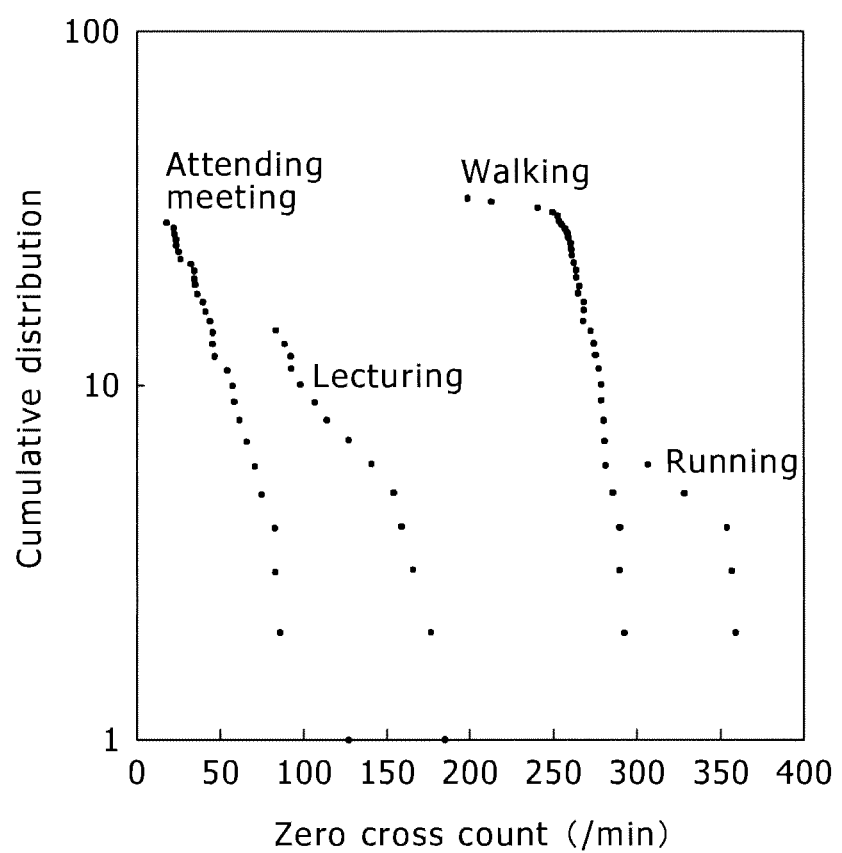
FIG. 8 is an example of the cumulative frequency distribution of the number of zero crossings of a worker according to the first embodiment.

As it is difficult to understand the trend only from this graph, the number of zero crossings occurring in each of the typical actions is shown in FIG. 8. FIG. 8 is a graph in which the horizontal axis represents the zero crossing number per 10 minutes obtained from the sensor, and the vertical axis represents the accumulative occurrence frequency. For example, the number 120 on the horizontal axis represents the number of times the zero crossing is equal to or more than 120. The number 120 corresponds to 1 Hz when it is converted to the frequency. Note that the vertical axis of the graph represents the log values. Further, the values of the horizontal axis show the values converted to per minute. The graph shows the level of the number of zero crossings in each of the four types of actions performed by a certain same worker. The four types include running, walking, lecturing, and attending meeting. When comparing each action with the others, it can be seen that the zero crossings numbers in running and walking are greater than the zero crossing numbers in lecturing and attending meeting in which the worker is mainly seated with a little movement.

Figure 9:
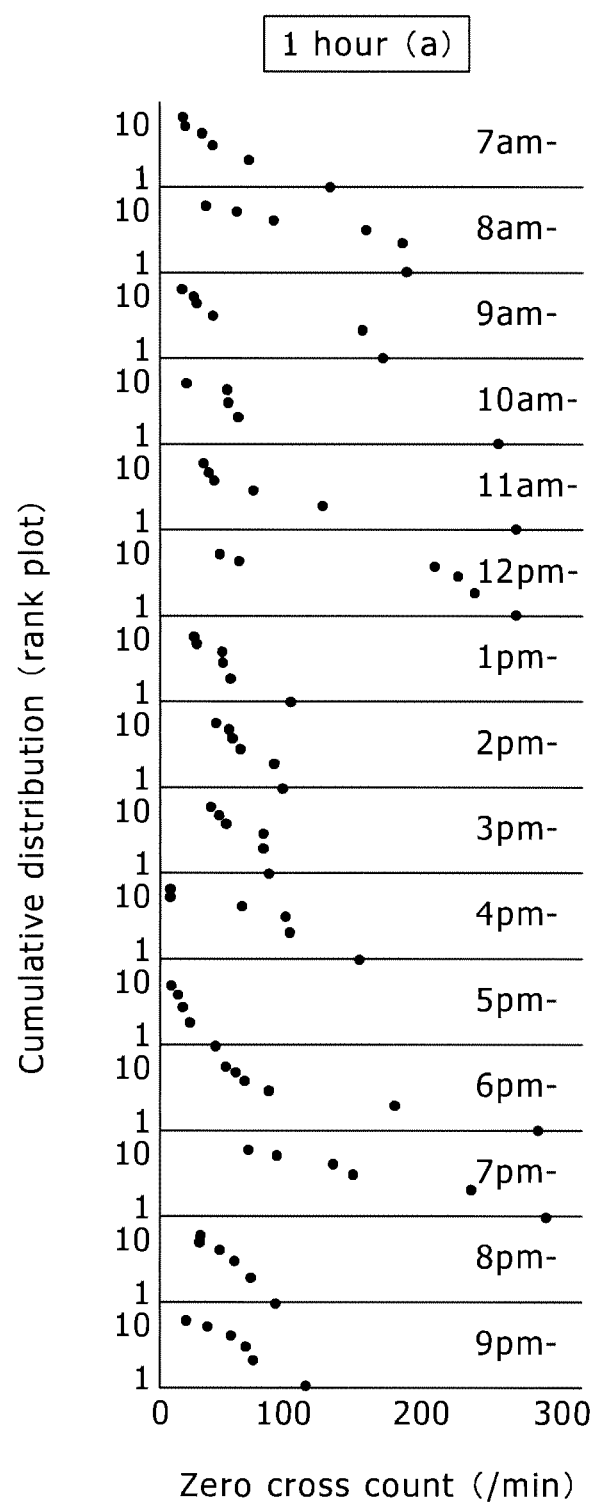
FIG. 9 is an example of the cumulative distribution of the number of zero crossings for every one hour of a worker according to the first embodiment.

Further, FIG. 9 shows the distribution of the number of zero crossings per hour in a certain day for a certain worker. When comparing each time period with others, for example, the zero crossing number is high at 8 o'clock when the worker is going to work, at 12 o'clock for lunch, and the like, which shows the state of the worker.

As described above, when focusing on a certain one-hour time period, and the like, of a certain action or a continuing series of actions, the zero crossing appearing in the particular time period varies, there is no common trend at a glance. This is not limited to the particular worker. From this fact, it can be considered that a relatively low zero crossing occurs by reflecting the intensity of a worker involved in many intensive operations, while a relatively high zero crossing is intensive for a worker involved in many conversation or business trips.

Figure 10:
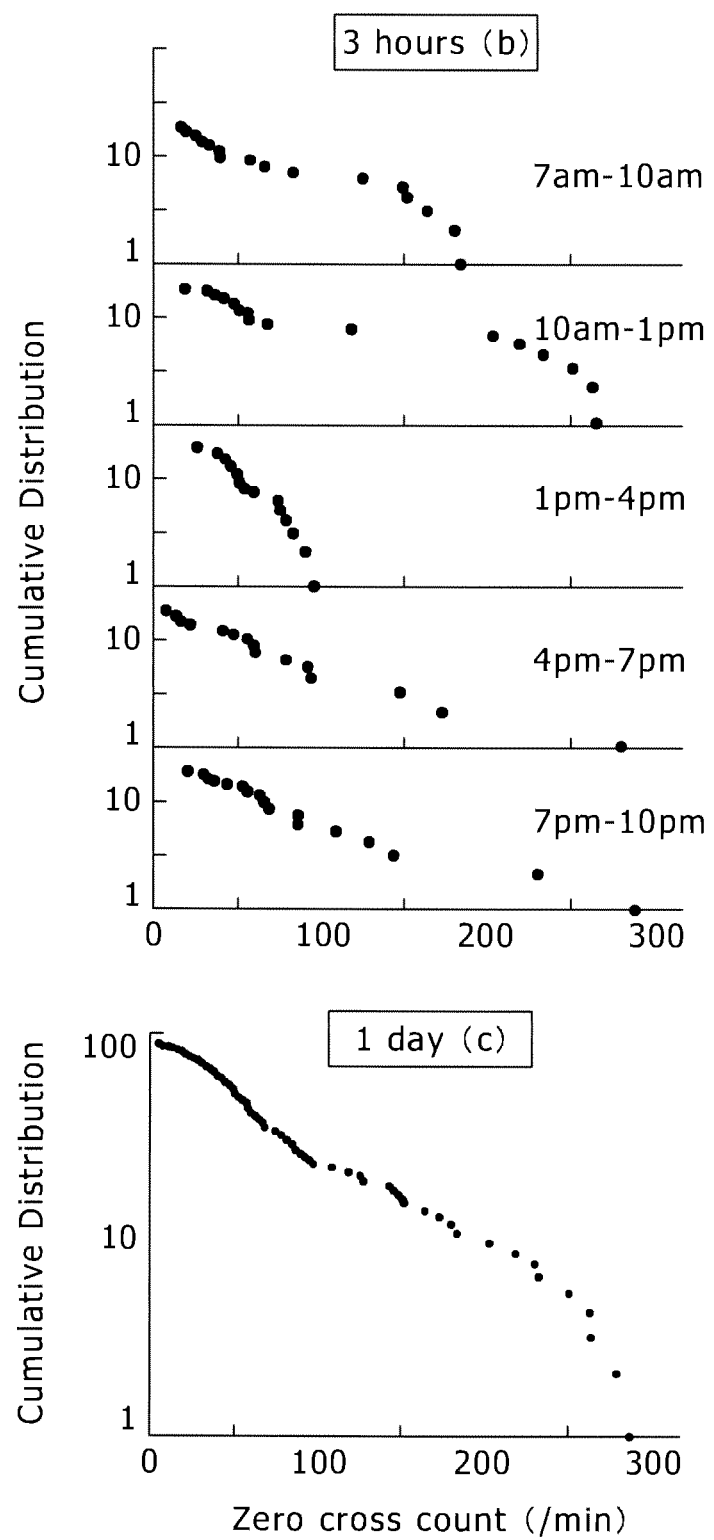
FIG. 10 is an example of the cumulative distributions of the number of zero crossings of a worker for every three hours and for one day according to the first embodiment.
Figure 11:
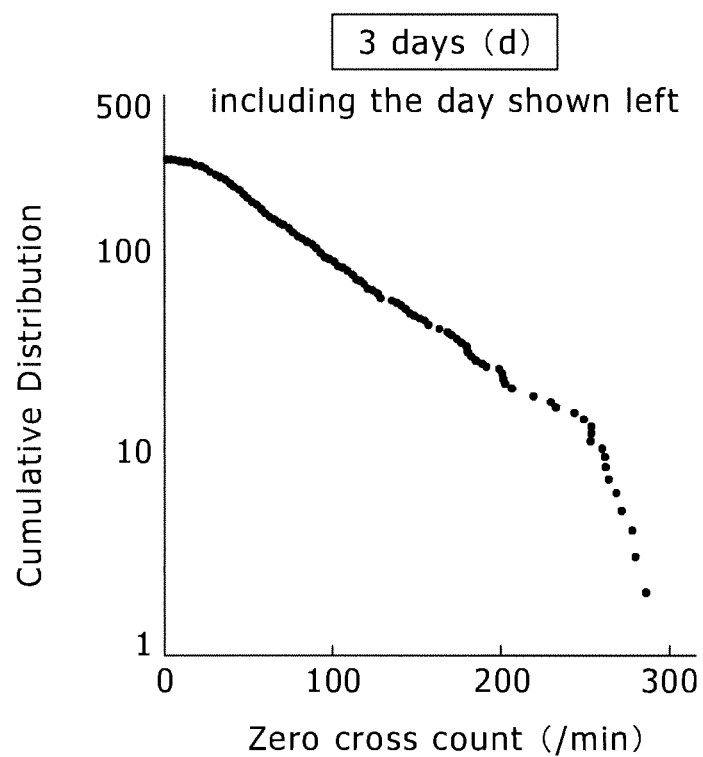
FIG. 11 is an example of the cumulative distributions of the number of zero crossings of a worker for three days and for two weeks according to the first embodiment.
Figure 11:
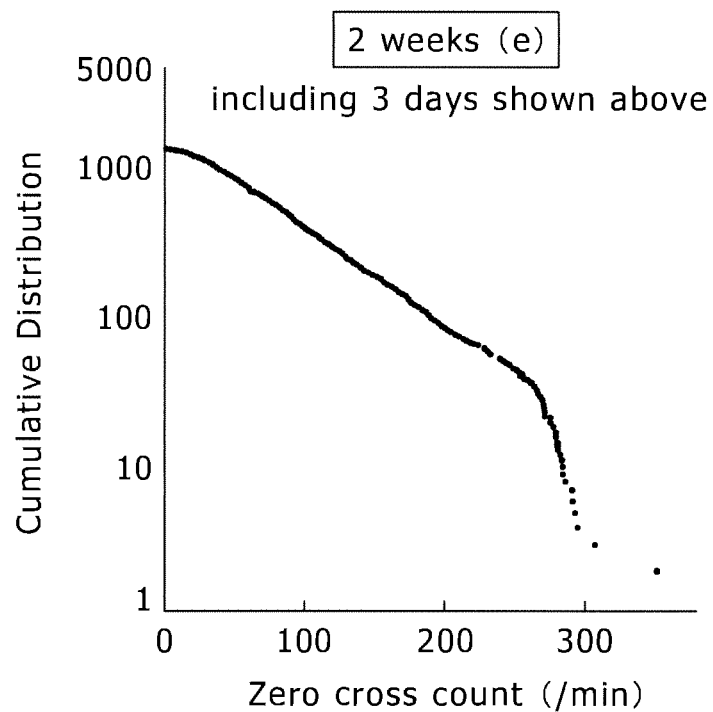

However, the present inventors have found out that a new trend can be seen by increasing the length of the time period for counting. The upper part of FIG. 10 is a graph in which the number of zero crossings is counted every three hours, and the lower part of FIG. 10 is a graph in which the number of zero crossings is counted for one day. Similarly, the upper part of FIG. 11 is a graph in which the number of zero crossings is counted for three days, and the lower part of FIG. 11 is a graph in which the number of zero crossings is counted for two weeks. It can be seen from these graphs that they have a tendency to linearly come down from the upper left to the lower right around the point where the number of zero crossings is counted for one day, and come down more sharply from the middle of the graph. The linearity of the graph is quite significant in the counting of three days and in the counting of two weeks.

Figure 12:
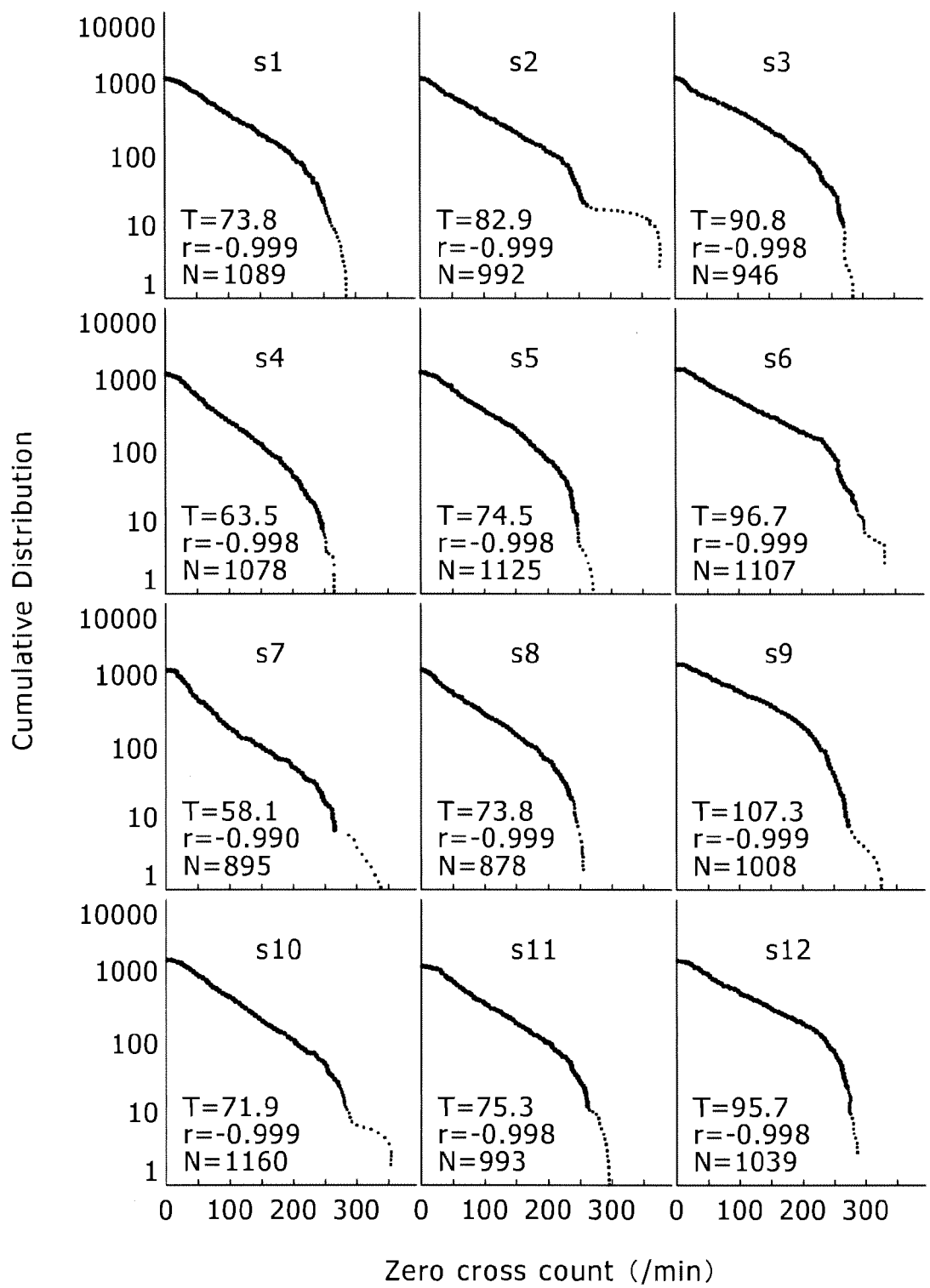
FIG. 12 is an example of the cumulative distributions of the zero crossing numbers of 12 workers according to the first embodiment.

Such a trend is not limited to a certain person. FIG. 12 shows the zero crossings numbers that are similarly obtained from twelve different workers s1 to s12. When comparing each zero crossing number with the others, it can be seen the common feature in which the graphs linearly come down commonly from the upper left point to the lower right and also down more sharply after a certain amount of activity, although the slope and the linearity of each graph is slightly different depending on each person. This commonality is apparently unintentional but is an astonishing result. This is because the examinees are a group of different ages, genders, and careers. There is a variety in the everyday work of the examinees, such as a person who has many business trips, a person who has many conversations, or a person who does mainly deskwork. Further, each person makes his or her own decision on how to spend after-work time and holidays. In other words, a certain amount of activity must be particularly large or small for each worker. In fact, as shown in FIG. 9 and others, when a graph for each hour and a graph for each action are plotted, the graphs reflects the particular action and are close to a certain zero crossing number. In this case, when the time period for counting is increased, the trend common to the entire distribution is apparent.

Figure 13:
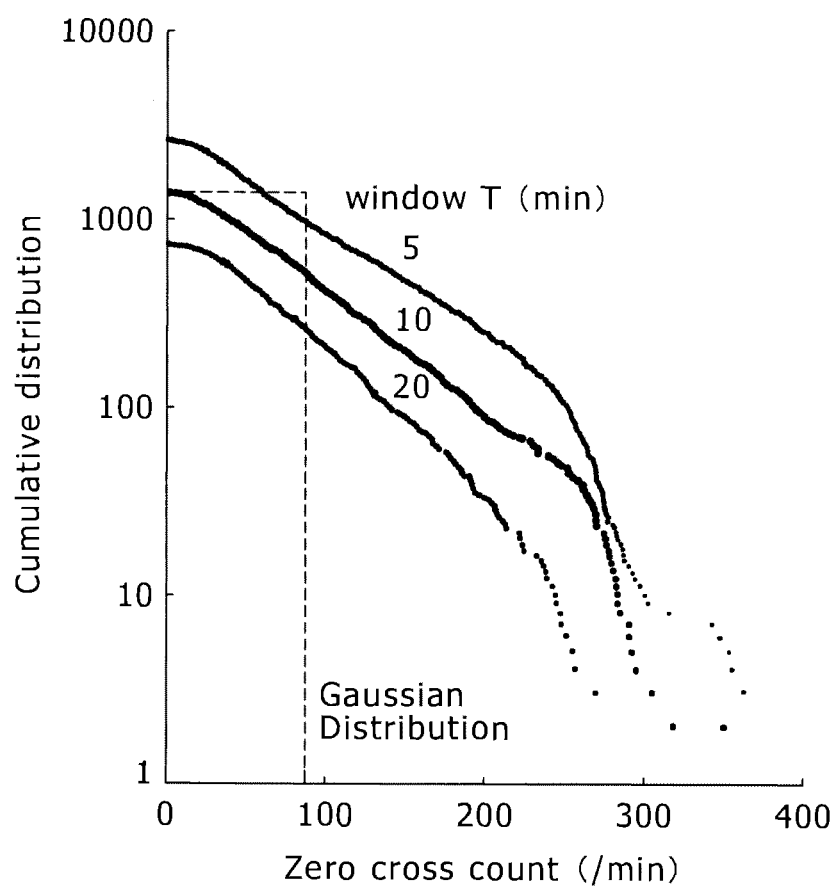
FIG. 13 is an example of the cumulative distribution of the number of zero crossings of a worker according to the first embodiment.

The above is the example of the distribution of the number of zero crossings obtained per 10 minutes. However, the time period for counting is not limited to 10 minutes. FIG. 13 shows the results of the counting of 5 and 20 minutes, in addition to the result of the counting of 10 minutes. As shown in the figure, the trend of both 5 and 20 minutes are the same as the trend of 10 minutes.

The following description will focus on four features as the communalities shown herein.

First is the degree of the slope of the part straight down from the most upper left to the lower right, which is referred to as a feature A (second feature data).

Second is the amount of activity (zero crossing number) when the slope greatly changes, which is referred to as a feature B (first feature data).

Third is the slope at an angle greater than the amount of activity shown in the feature B, which is referred to as a feature C (third feature data).

Fourth is the linearity of the segment of the part of the slope A, which is referred to as a feature D (fourth feature data). The four features are indexed in order to understand the difference between a certain worker and other workers, as well as the difference between a certain time period and other time periods with respect to the same worker.

A possible reason of such a common distribution is that the human energy is limited and it is difficult to perform only the action showing a high zero crossing number for a long time. Also, there may be other factors that influence the distribution. For example, Non-patent document 2 shows the fact that the human health condition is somehow related to the behavioral duration. More specifically, it has been found that the behavioral duration is different between depressed patients and healthy individuals from the statistical comparison. Similar to the method shown in the present invention, the number of zero crossings is obtained per minute from the examinees wearing sensors, to determine a certain zero crossing number as the boundary in order to define the zero crossing range above the boundary as the active state and the zero crossing range below the boundary as the inactive state. Next, each state is quantified to determine the length of the continuity. The states change such that the active state continues for 10 minutes in a certain time period, next the inactive state continues for 6 minutes, and then the active state continues for 2 minutes. Similarly, in Non-patent document 2, the results are shown as a graph, focusing on the frequency distribution of the duration. The results show the trend of the power distribution with a straight line drawn on the graph, in which the horizontal axis is the log of the duration of the inactive state and the vertical axis is the log of the ratio of the cumulative frequency. The remarkable result is that the slope of the line for the depressed patient is gentler than that for the healthy individual, with a high ratio indicating that the inactive state continues for a long time. However, there is no description of significant difference between depressed patients and healthy individuals with respect to the duration of the active state.

The features A to D according to the present embodiment can be effectively used as the index that indicates the human health condition as described in Non-patent document 2.

Figure 14:
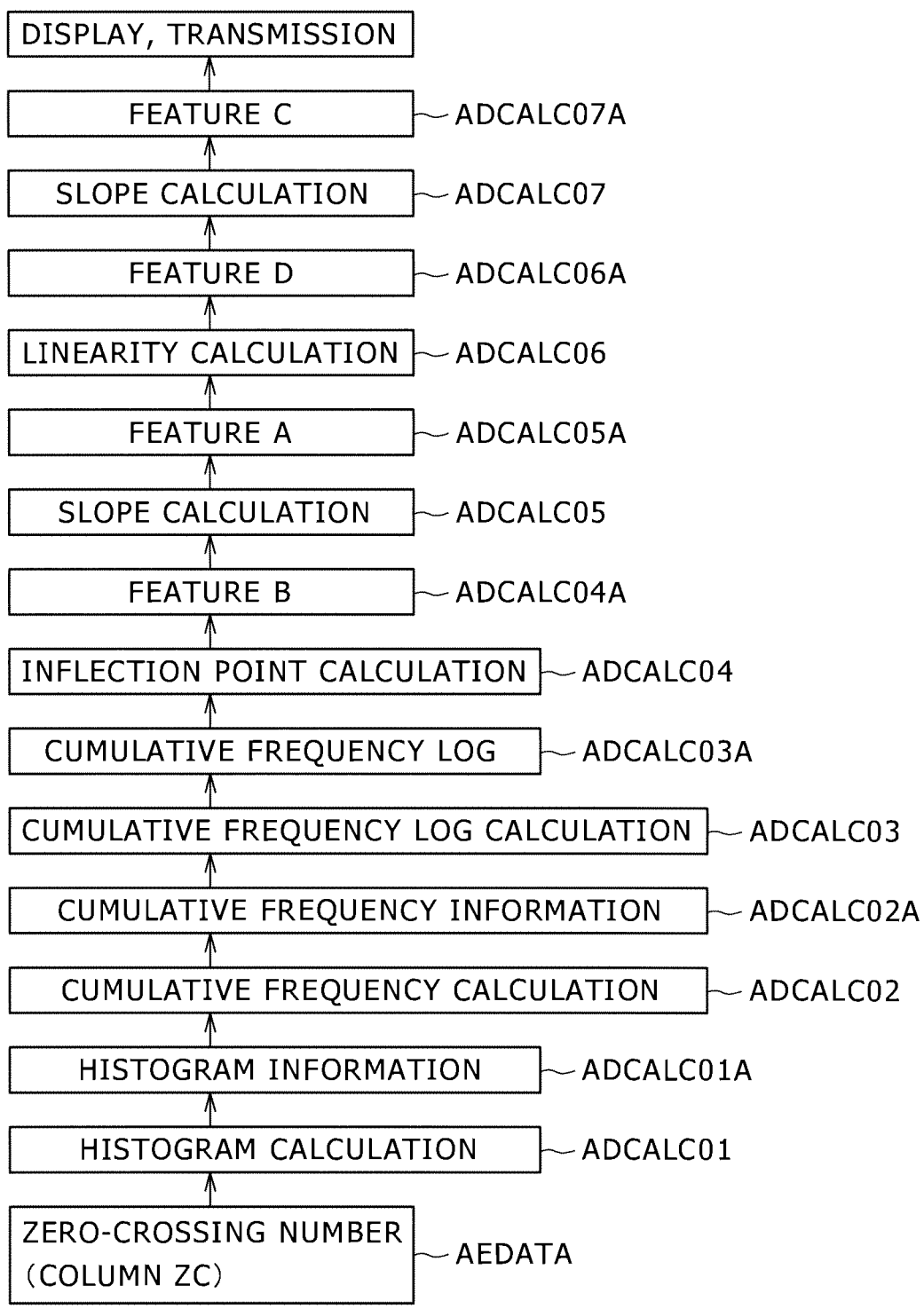
FIG. 14 is an example of the flow for calculating the feature of the distribution of the number of zero crossings of a worker according to the first embodiment.

FIG. 14 shows a flow of obtaining features A to D. As described above, each process of the flow is performed by the CPU2. The zero crossing number per minute calculated in FIG. 6 is input. For example, the zero crossing number may be read from the column AC of AEDATA. Here is an example in which the zero crossing number appears per minute as 12, 9, 5, 21, 61, 45, 16, 50, 2, 28, 42, and 35. This is a sample for a very short time of 12 minutes. The basic process for one day and for two weeks is the same as the process described above.

In a histogram generation ADCALC01, the system scans the zero crossing numbers per minute sequentially, and updates the part corresponding to a histogram information ADCALC01A. The system sets the width of one class of the histogram information ADCALC01A, for example, to the zero crossing number 20. In the example of the appearance describe above, the number of appearances is 5 in the range of 0 or more and less than 20, 3 in the range of 20 or more and less than 40, 3 in the range of 40 or more and less than 60, 1 in the range of 60 or more and less than 80, and 0 in the range above that.

Next, in a cumulative frequency calculation ADCALC02, the system calculates the cumulative frequency for each range. The cumulative frequency in a certain zero crossing number (reference value) X is the frequency with the zero crossing number equal to or more than X in the sample of all zero crossing numbers. As for the histogram information ADCALC01A, the cumulative frequency is 12 for the zero crossing number of 0 or more, 7 for 20 or more, 4 for 40 or more, 1 for 60 or more, and 0 for more than that. The range in which the cumulative frequency is 0 is excluded from the calculation target. The system stores the range of each class as well as the cumulative frequency of the range, in a cumulative frequency information ADCALC02A of the recording device DB1. Note that the reference value corresponds, for example, to the class of the histogram information. In addition to the method of obtaining a cumulative frequency by generating the histogram, any method can be used as needed to obtain the cumulative frequency for the reference value of a plurality of zero crossing numbers.

Figure 15:
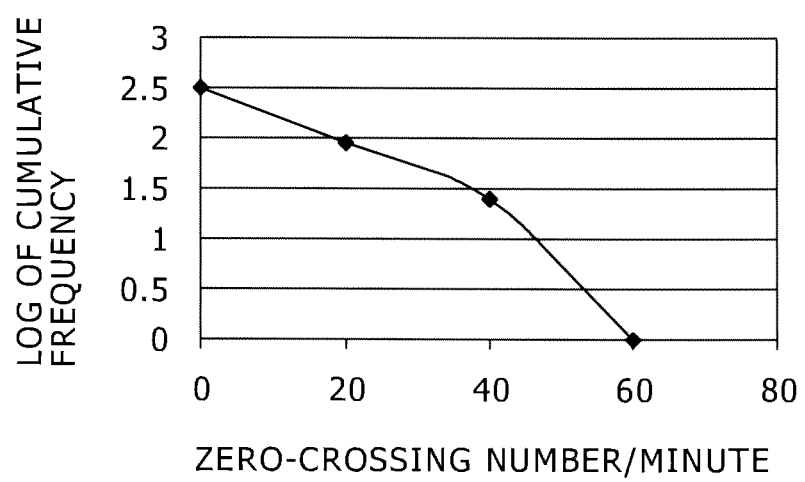
FIG. 15 is an example of the cumulative distribution of the number of zero crossings of a worker according to the first embodiment.

Next, in a cumulative frequency log calculation ADCALC03, the system calculates the log for each cumulative frequency of ADCALC02A. When the log of base 2 is calculated, for example, LN(12)=2.48 for the cumulative frequency 12. When it is calculated for the histogram described above, the log of the cumulative frequency is 2.48 for a zero crossing number of 0 or more, 1.95 for 20 or more, 1.39 for 40 or more, and 0 for 60 or more, respectively. The results are stored in ADCALC03A. FIG. 15 is a graph plotting the results.

Next, in an inflection point calculation ADCALC04, the system obtains the feature B, namely, the zero crossing number at which the line is highly curved on the graph shown in FIG. 15. Then, the system stores the result in ADCALC04A of the recording device DB1. For example, the system calculates and stores the inflection point by approximating the distribution between the reference value of the zero crossing number, and the log of the cumulative frequency for the reference value (which may also be referred to as the cumulative frequency distribution below) by a curved line or a plurality of straight lines.

It is desired to calculate about 40 zero crossing numbers on the graph. There may be several arithmetic methods for calculating the values. For example, there is a method of drawing the approximate line based on the values in the range from 0 to a certain number on the graph, and defining the zero crossing number at which the gap from the approximate value exceeds a certain threshold, as the inflection point. More specifically, as shown in FIG. 12, the distribution has linearity of about 200 zero crossing numbers. For example, it is possible to draw the approximate line by the values in the range from 0 to 200, obtain the zero crossing number at which the gap between the value obtained from the approximate line and the actual value is about 10% of one of the two values, and define the particular zero crossing number as the feature B. Another method is to calculate the second order differential equation in the graph to obtain the point at which the slope changes significantly. However, if the method is applied to data with a lot of noise, smoothing is necessary in advance by a moving average or other smoothing function. Here is shown another example of the calculation method based on the distance from the reference line.

Figure 16:
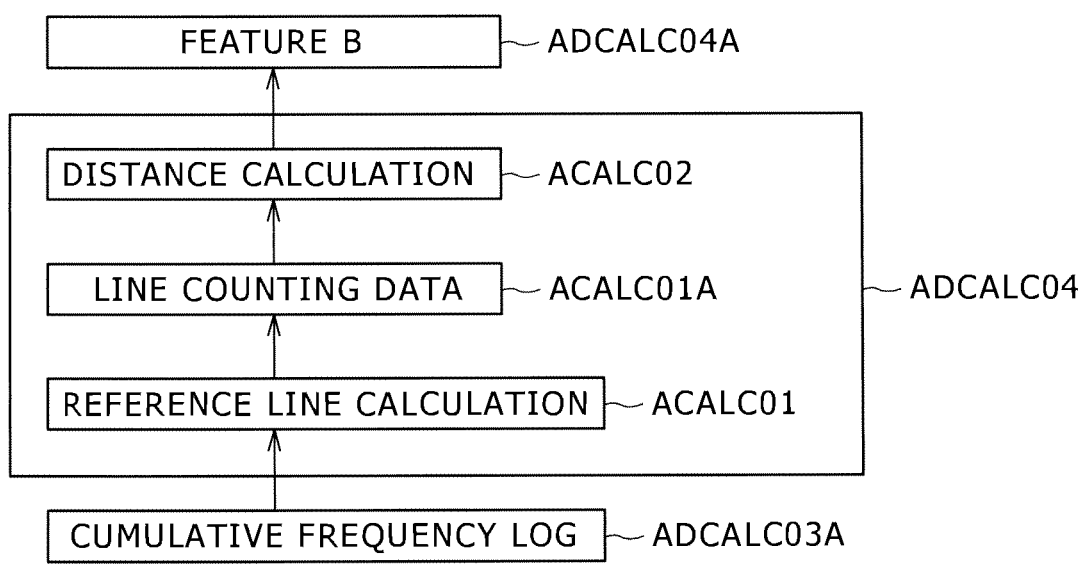
FIG. 16 is an example of the flow for calculating the inflection point of the cumulative distribution of the number of zero crossings of a worker according to the first embodiment.

FIG. 16 shows a calculation flow. In a reference line calculation ACALC01, the system obtains a line connecting the point of the cumulative frequency log with the zero crossing number 0 (YMAX), and the point at which the cumulative frequency log is 0 with the maximum zero crossing number (XMAX). Then, the count number of lines is stored in ACALC01A of the recording device DB1. The line passes through (0, YMAX) and (XMAX, 0) on the graph shown in FIG. 17. The line passing through the two points on the graph is given by y−YMAX=(0−YMAX)/(XMAX−0)*(x−0) based on the common formula. The equation is transformed into YMAX*x+XMAX*y−YMAX*XMAX=0. The count number of lines is the value of a, b, c, when the line is expressed by the equation ax+by+c=0. In the above equation, a is the value of YMAX, b is the value of XMAX, and c is the value of −YMAX*XMAX. The line is shown by ACALC01B in FIG. 17. Here, it is focused on the fact that the point at which the gentle slope changes to a steep slope is generally the most distant from the reference line. Thus, as described below, the system obtains the distance between each point and the reference line to define the zero crossing number with the longest distance, as the feature B. Because the gentle slope changes to a steep slope, the graph is convex up. Sometimes a part of the actual value may be below the reference line due to noise or other factors, which is excluded from the distance calculation target.

In a distance calculation ACALC02, the system calculates the distance between the reference line and each point on the graph. Then, the system stores the zero crossing number of the point at which the distance is the largest, into ACALC02A of the recording device DB1 as the feature B. When the common formula for calculating the distance between a line and a point, the distance between the reference line and a certain point (X0, 0) can be obtained from ABS(YMAX*X0+XMAX*Y0−YMAX*XMAX)/SQRT(YMAX*YMAX+XMAX*XMAX). Here, ABS means a function of an absolute value, and SQRT means a function for calculating the square root. Practically, it is enough to obtain the magnitude relationship of distances, so that the calculation of the denominator, which is the common part, and the calculation of YMAX*XMAX may be omitted.

Figure 17:
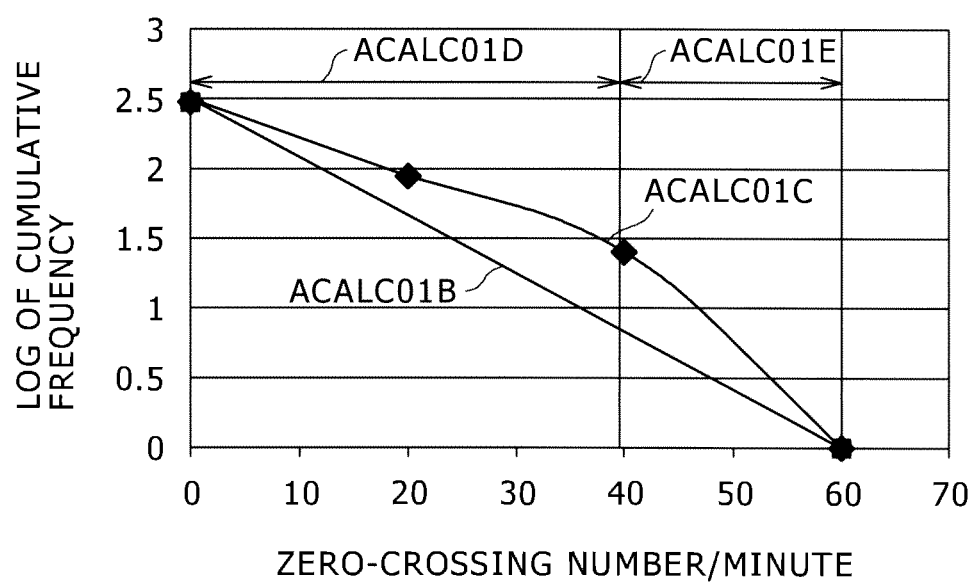
FIG. 17 is an example of the cumulative distribution of the number of zero crossings of a worker according to the first embodiment.

The distance from the reference line to each point on the graph shown in FIG. 17 is calculated, and the following results are obtained: 0 for the zero crossing number 0, 0.29 for 20, 0.56 for 40, and 0 for 60. In a longest distance calculation ACALC03, the system identifies the point at which the distance is the longest. In this way, the feature B is calculated as the zero crossing number 40 and is stored.

Now returning to FIG. 14, the process of a slope calculation ADCALC05 and the subsequent process will be described. In ADCALC05, the system calculates the feature A, namely, the slope of the straight line segment (first approximate line) in the part in which the zero crossing number is low in the cumulative frequency distribution. Then, the result is stored in ADCALC05A of the recording device DB1. This corresponds to the slope in the range of ACALC01D in FIG. 17. In this case, the value of the feature B obtained by the flow shown in FIG. 17 can be used. In the cumulative frequency graph, the system obtains an approximate line in the range in which the zero crossing number is the value of the feature B, from the zero crossing number 0. In other words, the system obtains a line with the highest approximation for all coordinates of (0, YNAX), (X1, Y1), (X2, Y2), (the feature B, the log of the cumulative frequency for the feature B). It can be calculated, for example, by the common method of least squares so that the sum of squares of the prediction error in the y coordinate is the smallest. Further, as a simple method of calculation in a sensor device with a small amount of calculation resources, it is possible to calculate the slope of the line passing through only two points of (0, YMAX) and (the feature B, the log of the cumulative frequency for the feature B), instead of the common method of least squares. In other words, the feature A=(the log of the cumulative frequency for the feature B−YMAX)/(the feature B). In the example shown in FIG. 17, the feature A=(1.38−2.48)/40=×0.027.

Next, the process of a linearity calculation ADCALC06 will be described. In this process, the system calculates the linearity in the part where the zero crossing number is low in the cumulative frequency distribution, and stores the result in ACALC06A of the recording device DB1. For example, the system calculates the degree of linearity of the part of ACALC01D in FIG. 17. If the distribution of this part is an exact straight line, the degree of the linearity is considered to be high. If the distribution varies up and down away from the line, the degree of linearity considered to be low. There are considered several options to indicate this. The simplest is to calculate the correlation coefficient of a pair of x coordinates and a pair of y coordinates in the range in which the zero crossing number is the value of the feature B, from the zero crossing number 0 in the cumulative frequency graph, by using the value of the feature B obtained by the flow shown in FIG. 14. It is assumed that the feature D is obtained by multiplying the correlation coefficient by −1 because the slope of the line is negative. If there is perfect linearity, the correlation coefficient is −1 and the feature D is 1. If there is no linearity, the feature D is 0. More specifically, if the points (0, YMAX), (X1, Y1), (X2, Y2), (the feature B, the log of the cumulative frequency for the feature B) are present in the range from the zero crossing number to the feature B, the system calculates the correlation coefficient of a pair of x coordinates (0, X1, X2, the feature B) and a pair of y coordinates (YMX, Y1, Y2, the log of the cumulative frequency for the feature B), and stores the result. In the example shown in FIG. 15 (FIG. 17), the feature D=0.99994.

The next shows a slope calculation process ADCALC07. In this process, the system calculates the feature C, namely, the slope of the straight line segment (second approximate line) in the part where the zero crossing number is high in the cumulative frequency distribution, and stores the result in ADCALC07A of the recording device DB1. This corresponds to the slope of the part of ACALC01E in FIG. 17. In this case also, it is possible to use the value of the feature B obtained by the flow shown in FIG. 16. The system can calculate the approximate line in the range of zero crossing numbers from the value of the feature B to the maximum value actually detected. In other words, the system calculates the straight line with the highest approximation for all coordinates of (the feature B, the log of the cumulative frequency for the feature B) (X1, Y1) (X2, Y2), (XMAX, 0). Similar to the method described above, it can be calculated by the common method of least squares so that the sum of squares of the prediction error in the y coordinate is the smallest. Further, as a simple method of calculation in a sensor device with a small amount of calculation resources, it is possible to calculate the slope of the line passing through only two points of (the feature B, the log of the cumulative frequency for the feature B) and (XMAX, 0), instead of using the method of least squares. In other words, the feature C=(the log of the cumulative frequency for −1*the feature B)/(XMAX−the feature B). In the example shown in FIG. 17, the feature C=(0−1.38)/(60−40)=−0.069.

Examples of the processes for obtaining features A to D have been described above. However, other indices can also be obtained as an index for characterizing the cumulative distribution graph. For example, similar to the feature D, the linearity of the straight line segment can be obtained in the part where the zero crossing number is high. Further, similar to the feature A, the slope of all approximate lines can be obtained by combining the high part and the low part. Also, similar to the feature D, the linearity can be obtained for the entire distribution. It is also possible to obtain the difference in the slope between the part where the zero crossing is low and the part where the zero crossing is high, for example, as the difference between the feature A and the feature C.

FIG. 14 is an example of obtaining feature values of the distribution. In this example, the inflection point calculation ADCALC04 is performed to divide the distribution into two parts: a first part where the zero crossing number is below the inflection point; and a second part where the zero crossing number is above the inflection point, in order to obtain the slope and linearity in each part. It is also possible to divide the distribution by using the average zero crossing number, and the like, instead of obtaining an inflection point. In this case, it is possible to generate features of the slope of the entire range, the slope of the approximate line range below average (third approximate line), the slope of the approximate line range above average (fourth approximate line), and the difference between the slope below average and the slope above average.

Health Condition Estimation System

The next shows an exemplary embodiment of a system for estimating the human health condition by using the indices such as the features A to D obtained as described above.

Figure 18:
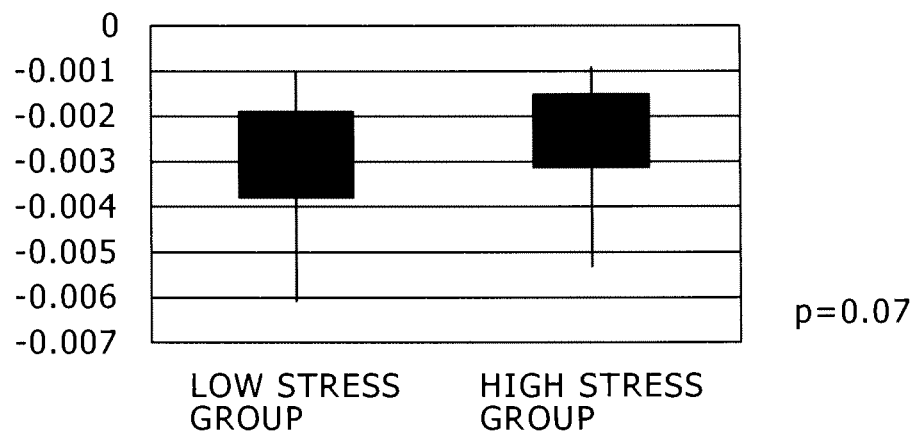
FIG. 18 is an example of the estimation results of stress according to the first embodiment.
Figure 18:
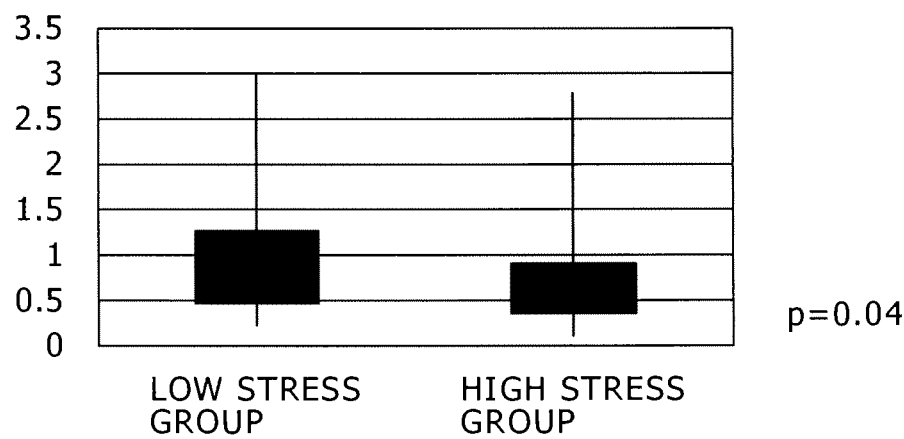
Figure 18:
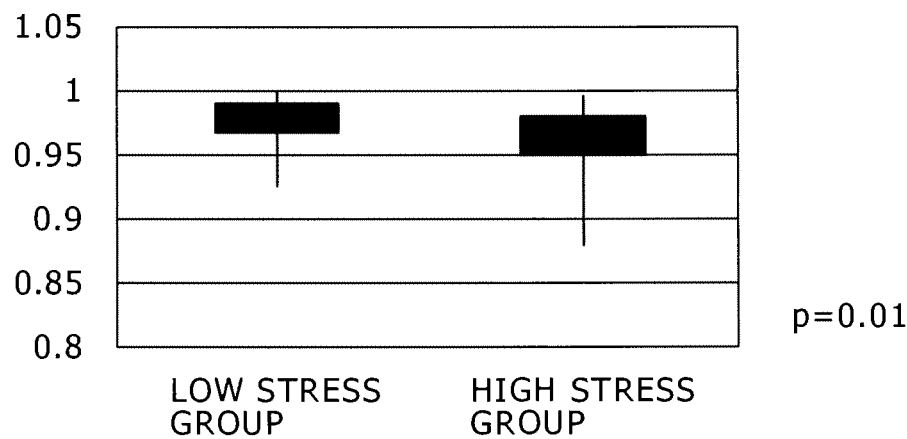

Before describing the system in detail, the analysis result of the relationship between the features A to D as described above and the human health condition is first shown. In the experiments conducted by the inventors, a questionnaire survey was conducted to measure the stress level while measuring 75 examinees by their name-tag type sensors for one month. The stress questionnaire is typical and is called CES-D. CES-D evaluates the magnitude of stress, namely, the risk of mental health patients, in 60 stages. In general, 26 and hither stages are considered to be high stress and others are considered to be low stress. As a result of the questionnaire, it is determined that 48 out of 75 persons are a high stress group, and 27 persons are a low stress group. FIG. 18 is the results of the analysis of whether there is a statistical difference between the two groups when the above features are calculated for the two groups. As a result of the analysis of variance, for example, the difference in the feature A between the two groups appears as a small difference, although the statistical significance, p value, is about 0.07 and is slightly higher than p=0.05, which is the level considered to be significant. There is a difference in the statistical significance between the features B and D (p=0.04, 0.01). In the feature B, the high stress group is smaller than the low stress group. In other words, when the stress is high, the appearance frequency of a certain amount of activity or more rapidly decreases. In the feature D, the linearity is lower in the high stress group than in the low stress group. This shows that the amount of a certain activity is sometimes increases and sometimes decreases and the deviation is large. As described above, it is found that the typical distribution of the amount of activity in human behavior is shown by a very small number of features, at most only 4, which represents the human internal state such as stress, in the range of the experiments.

Figure 19:
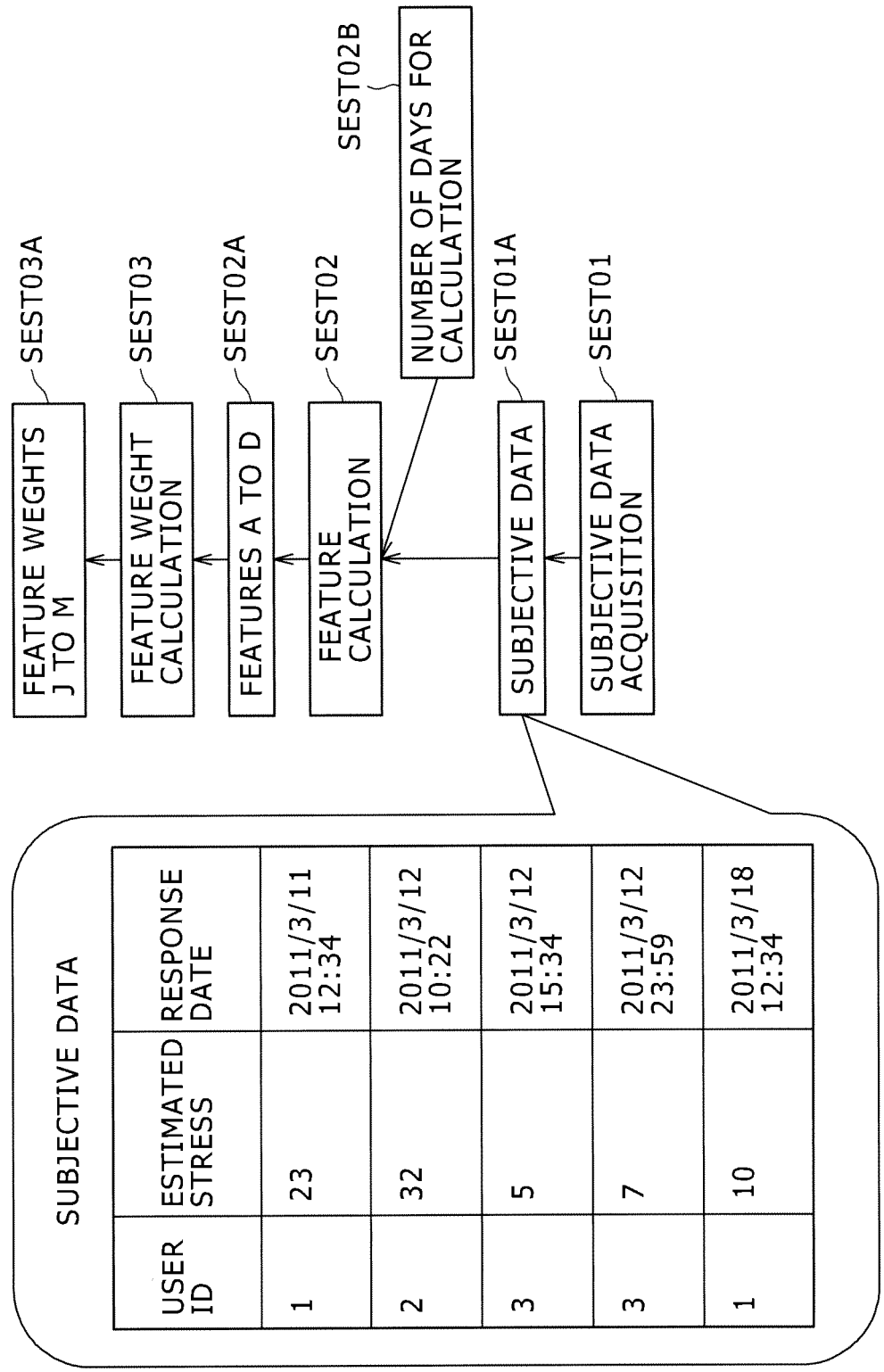
FIG. 19 is an example of the flow for estimating the stress value of a worker according to the first embodiment.
Figure 20:
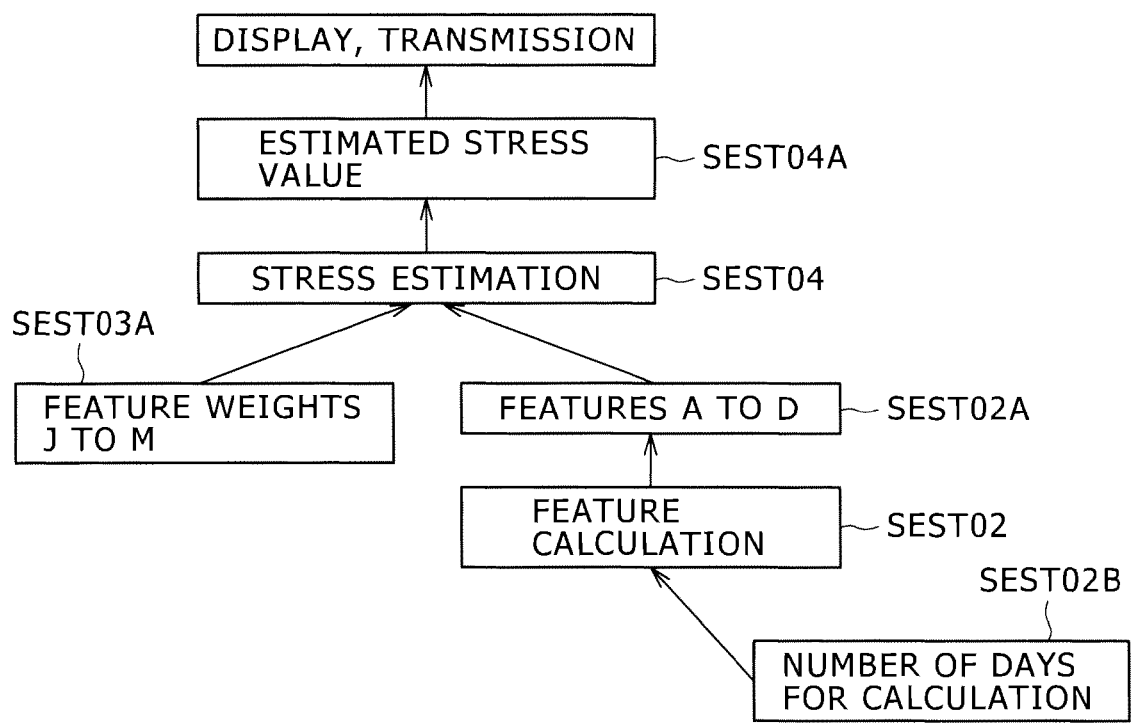
FIG. 20 is an example of the flow for estimating the stress value of a worker according to the first embodiment.

Based on this result, a program SEST for estimating the human stress level can be performed by the flows shown in FIGS. 19 and 20. First, in a subjective data acquisition process SEST01, the system obtains the stress level of each user by a questionnaire. Then, the system counts the stress value (for example, CES-D value) from the obtained information, and stores the stress value in a subjective data SEST01A of the recording device DB1, together with the user ID and the user questionnaire input date (response date). The questionnaire can be answered on the Internet web site, or can be collected via email or other means. The results of the questionnaire are summarized by a predetermined method according to the conducted questionnaire. In the case of the CES-D questionnaire, the user is allowed to answer in four stages from 0 to 3. It is known that the subjective stress value can be calculated by summarizing the results of the questionnaire. Note that the previously requested stress value can be read from the recording medium, input from an input part and the like, or received from the other device through a communication line.

Next, in a feature calculation process SEST02, the system calculates the values of the features A to D by the method described above, and stores calculation result SEST02A. The time period to be calculated is the data of a certain time period including the questionnaire response date stored in the subjective data SEST01A. The length of the time period is set, for example, prior to the process of SEST02 by a calculation parameter SEST02B. For example, the time period to be calculated is stored per day. If the number 10 is stored, the system calculates the index by using all data from the data obtained 10 days ago from the start of the estimation, to the data of the calculation date. The number can be set in advance by the system developer. It is also possible to change the number by the user of the system by adding the attributes of the user's operation.

Next, in a feature weight calculation process SEST03, the system calculates a parameter for estimating the subjective stress value like the one stored in SEST01A, from the given features A to D and the given stress value. Then, the system stores the result in an estimation parameter SEST03A. There are various statistical methods for estimating one variable by using a plurality of variables, which can be used in this process. For example, weight coefficients can be obtained for each person to be measured so that the sum of the error between the estimated stress value obtained based on the obtained feature data A to D and on the weight coefficients J, K, L, M for each of the feature data A to D, and the input stress value is small. Simply, the weights of the features A to D can be calculated from the multiple linear regression analysis. In other words, it is assumed that the estimated value $EST_i$ of the subjective stress of a certain user i can be calculated from the values ($A_i$ to $D_i$) of the features A to D of the user i, and from the weights (J to M) for the values Ai to Di, such as $ESTi=J*Ai+K*Bi+L*Ci+M*Di$. It is possible to calculate the values of J to M for each user, but in this embodiment, the system assumes that the values of J to M are common to all users and stores in SEST03A. For example, in the case of the user group where the features B, C are related to the stress and the features A, D are less related to the stress, the obtained result is that the values K and L are higher than the other values J and M, such as J=1, K=2, L=2, and M=0.5.

Once the feature weight SEST03A is obtained, the system can perform a stress estimation process SEST04 for a predetermined user without taking the questionnaire. The process flow is shown in FIG. 20. In SEST04, the system calculates the features A to D (SEST02A) of the target user. Then, the system calculates and stores an estimated stress value SEST04A of the target user, by using the calculated features A to D, and by using the information of the estimation parameters (J to M) SEST03A calculated as shown in FIG. 19. As described above, when the estimated value ESTi of the subjective stress is modeled by the equation $ESTi=J*Ai+K*Bi+L*Ci+M*Di$, it is possible to calculate ESTi by substituting the actually calculated results SEST02A into Ai to Di, and by substituting the information of the estimated parameters SEST03A into J to M. Note that there may be a plurality of target users i. In this case, the system obtains the estimated stress value for each of the users.

In order to perform the estimation with high accuracy, it is desirable to perform the processes from SEST01 to SEST03 in advance by collecting information on a certain number of users. For example, the system measures the data from about 30 users, and then performs the processes from SEST01 to SEST03. In the example of the flows shown in FIGS. 19 and 20, once M is estimated from J, the value is not changed and the stress estimation process SEST04 is performed according to the request of the user or by the system periodically. As another example, it is also possible to obtain the questionnaire information SEST01 as needed, and estimate the estimated parameters SEST03A each time SEST01 is obtained. This requires the calculation time for update, but increases the ability to calculate the estimated value more accurately.

Further, in the case of a plurality of users, the feature weight SEST03A common to all the users can be calculated by the flow shown in FIGS. 19 and 20. On the other hand, if the behavior of a same user is measured for a long time and the user can answer the questionnaire repeatedly, it is possible to calculate the feature weight for each particular user. Thus, a further increase in the estimation accuracy can be expected. In this case, it is possible to record the feature weight SEST03A for the number of users and store each feature weight together with the ID information of each user. In the stress estimation process SEST04, the system can calculate the estimated stress value SEST04A by referring to the corresponding part of the feature weight SEST03A based on the corresponding user ID information.

The estimation method based on the subjective questionnaire on the stress level called CES-D has been described. However, the present invention is not limited to such a specific questionnaire. Any other questionnaires for surveying the internal state demonstrated in the human behavior can be widely used. In particular, it is highly compatible with the questionnaire correlated with CES-D, such as stress level, tendency of depression, mental disorder, and fatigue, or the questionnaire negatively correlated with CES-D, such as degree of happiness, degree of fulfillment, job satisfaction, and teamwork. Further, it is also possible to use data reflecting these internal states, such as business productivity and sales performance, instead of the questionnaire on the human internal state.

Figure 21:
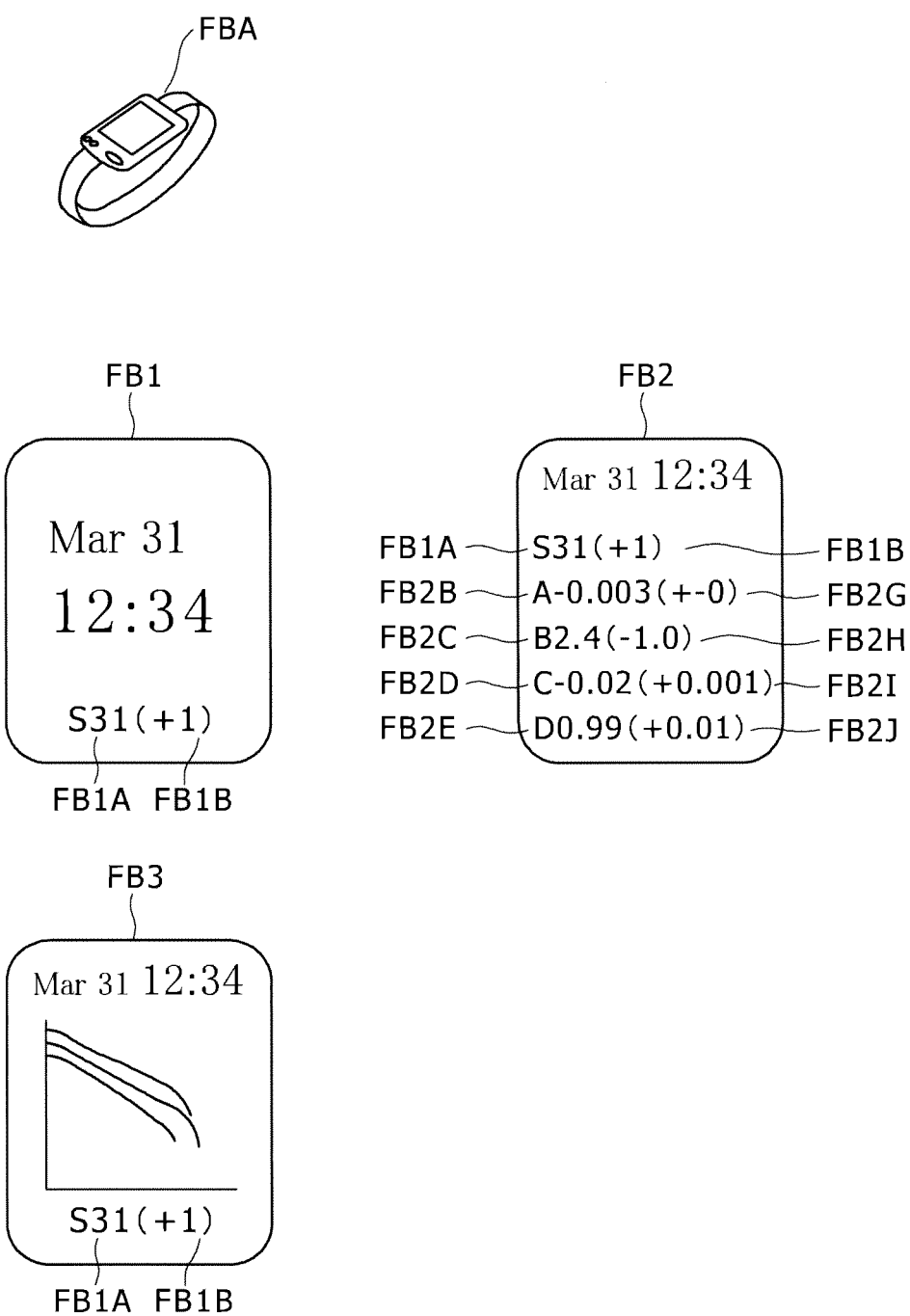
FIG. 21 is an example of the information feedback to a worker according to the first embodiment.

The next shows an example of the feedback of the features A to D and the estimated stress value, which are calculated as described above, to the user. As described in the beginning of this specification, one of the main objects of the present invention is to provide information to the user in a small device with a small area for displaying data, such as a wristwatch and a name tag. FIG. 21 is an example of a typical display, showing example of the device displayed on a device FBA. One of the screen examples FB1 to FB3 is displayed on the device. One of the screens FB1 to FB3 can be displayed constantly, or all the screens FB1 to FB3 can be displayed sequentially by a button and the like mounted on the FBA. In the screen FB1, the last estimated stress value for a predetermined time period is shown as FB1A, in addition to the information on the time. The time period for calculation is determined by referring to the parameter SEST02B as described above. For example, the stress value is estimated for the data for 10 days until the previous day of the day to be displayed. The user refers to the value to determine whether his/her own stress is high or low. If the stress is high, the user can have a break or enjoy sports and leisure time to relieve stress. Further, in addition to the estimated stress value, it is also possible to display the increase and decrease of the estimated stress value in numbers and images. For example, if the stress value is increased by one from the last time period to be measured, this can be displayed as FB1B. It is possible to determine the increase and decrease by comparing the currently displayed target time period with the past time period, and by calculating the amount of the change in the estimated stress value. For example, the current estimated value can be calculated by the behavior information for 10 days until the previous day of the day to be displayed, while the past estimated value can be calculated by the behavior information for 10 days from 11 to 20 days before the day to be displayed.

The screen FB2 is an example of displaying the values of the features A to D, which are the basis of the estimated stress value, as well as the increase and decreases of the estimated stress value, in addition to the estimated stress value. The features A to D can be displayed as FB2B to FB2E, and their increase and decrease can be displayed as FB2G to FB2J, respectively. For users who understand the meaning of the features A to D, it is possible to urge them to take more appropriate action by displaying the information on the screen FB2. For example, if the feature B is low, the user can understand that the action with a high zero crossing number reduces and can actively do sports or other activities with a high zero crossing number. Further, considering the reason why the user may not do an activity with a high zero crossing number, it is possible to change, for example, the work assignment so that the work load is reduced.

The screen FB3 is an example of the display using an image instead of numbers. As shown in FIG. 15, the system calculates the distribution of the number of zero crossings and displays curves. Image feedback may allow the user to easily and intuitively understand the whole trend and features, although the exact numbers are unknown. Further, it is also possible to display not only the curve of the latest time period but also the curve of the past time period. The line color and width can be changed in order to increase the visibility.

Variation

Figure 22:
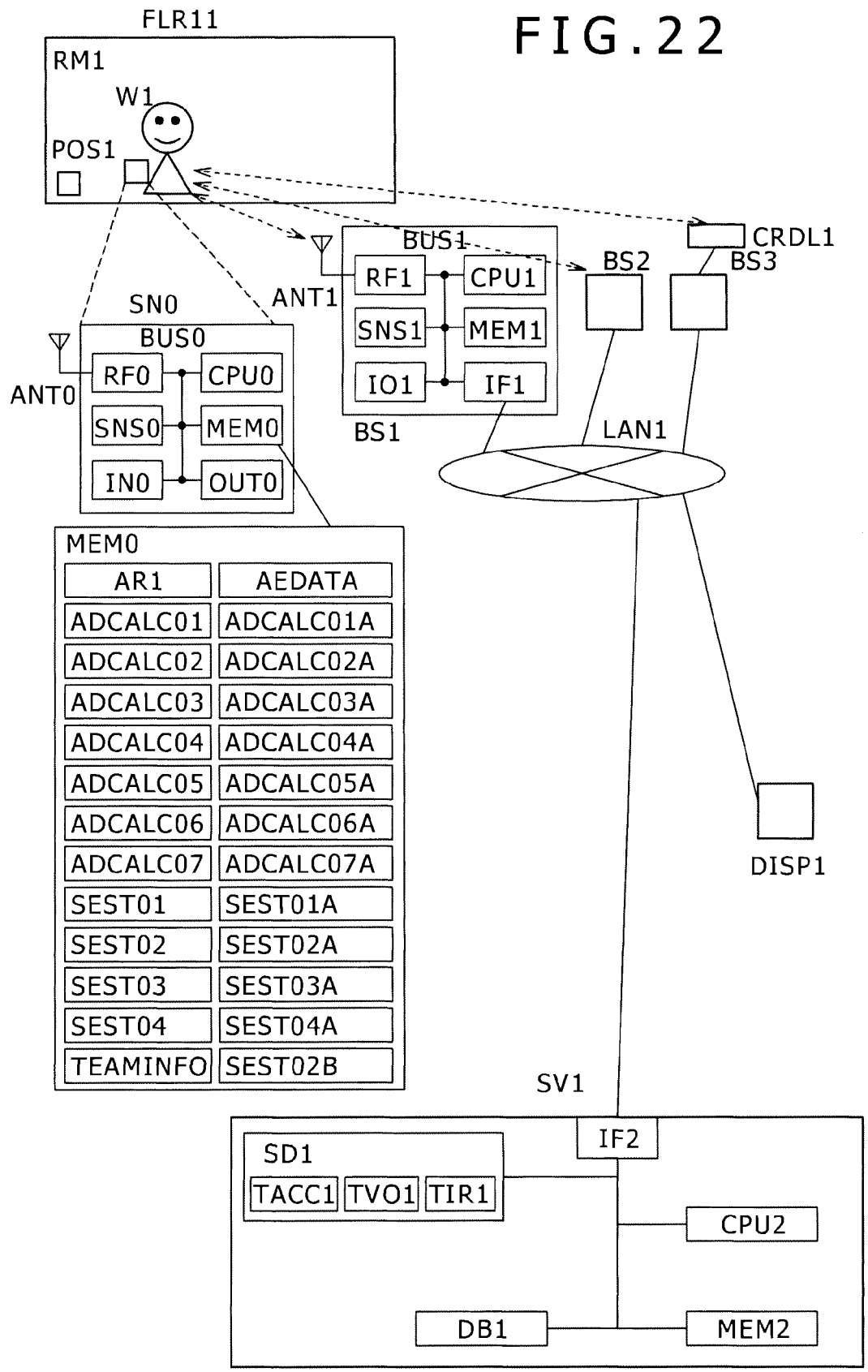
FIG. 22 is an example of the general configuration of a system for performing feature calculation and stress estimation on a sensor node.

As described above, the system obtains data by the device SN0 and transmits the result to the server SV1. Then, the system performs data processing and stress estimation on the server SV1 with high calculation ability, and generates feedback information. Then, the system transmits the result to the device SN0, and provides the result to the user by means of email and the Internet. The data processing and display is not necessarily performed on the particular device, and can also be performed on other hardware. For example, if the calculation ability of the device SN0 is high, it is possible to perform data processing and stress estimation on SN0, and transmit only the result to the serer SV1. The configuration of the system is shown in FIG. 22.

Further, the above description is an example of providing feedback to the user wearing the device SN0. However, the feedback can also be output to the display device if needed. It is also possible to provide data to a person other than the user, or provide data by combining data of a plurality of users. An example of providing data to a person other than the user is that, for example, when ill or elderly person wears the device, doctors and family members see the result displayed on the device, so that treatment and care may be facilitated. In order to achieve this, the system stores the ID of the device worn by the person, together with the contact information of the person who receives the information as well as the information of browse equipment. Then, the system automatically provides the information to the appropriate person via email or web browser.

An example of providing data by combining data of a plurality of persons is that, for example, when a plurality of workers wear the device in a certain department of a company, the manager of the department can understand the average stress level of the department as well as the person with a high estimated level of stress in order to perform appropriate management. In this case, similar to the above case, the system stores the ID of the device worn by the worker, together with the contact information of the person who receives the information as well as the information of the browser equipment. The system estimates the stress level of all the users in the department. Then, the system averages the results and provides feedback to the manager via email or web browser. Further, when the manager wears the device, it is also possible to transmit the information of the average stress value of the department to the device of the manager and display the information. As a result, the manager can reduce the volume of business of the entire department or a particular individual, and can plan activities to relieve stress.

2. Second Embodiment

In the first embodiment, the system is designed to calculate the indices of the features A to D from the distribution of the number of zero crossings to estimate the stress value based on the indices. The present embodiment can be applied not only to the distribution of the number of zero crossings with the features A to D, but also to a distribution with a trend common to different persons in which the slope and linearity of the line are included in the features of the distribution. As an example of the present embodiment, the measurement of the features of the distribution of the duration of behavior will be described below.

In Non-patent document 2 described above, it has been found that when the duration of behavior is statistically compared between depressed patients and healthy individuals, the duration of behavior is different between them. A certain zero crossing number is defined as the boundary. Then, the region above the boundary is defined as active state and the region below the boundary is defined as inactive state. Next, the continuity of the appearance of each state is quantified, which shows the result of graphing the frequency distribution of the continuous time period. When the horizontal line represents the log of the continuous time period of the inactive state and the vertical axis represents the log of the ratio of the cumulative frequency, a line is drawn on the graph. Particularly, in the case of the depressed patients, it is found that the slope of the line is gentler than that of the healthy individual, and that the ratio in which the inactive state continues for a long time is high. On the other hand, with respect to the duration of the active state, a line is not shown on the graph, so that the slope of the line or other features is not quantified. There is no description on a large difference between depressed patients and healthy individuals.

The present inventors have focused on the possibility that the features of the graph might be calculated and used for stress estimation as described above. Also, the present inventors were aware of the possibility that the accuracy of the estimation increases by breaking down activities into smaller pieces and calculating the duration of each activity, instead of simply treating all activities as the same and calculating the duration of the activities as a whole. There are several methods of breakdown. The present inventors have focused on communication activity. Communication is one of the main factors of stress. Further, the present inventors have focused on the possibility that communication requires larger energy than that of individual activity and is likely to vary depending on stress. This can be seen from the opposite. A person communicating with the other person worries about what the partner thinks or feels, and may make an effort to be more pleasant despite bad health condition. However, a person who is involved in an personal work may behave naturally without worrying about other people's eyes. In such a case, if the data of communication activity is included, noise occurs preventing the stress from being accurately estimated. It is difficult to discriminate between communication activity and individual activity by the sensor with only the acceleration sensor as described in Non-patent document 2. On the other hand, the determination of the activity is possible by the name-tag type device with infrared communications as described above. Further, in the system described above, one value is used in the discrimination between the active state and the inactive state. The present inventors have focused on the possibility that more accurate estimation can be achieved by providing some standards for the determination of active or inactive state.

Figure 23:
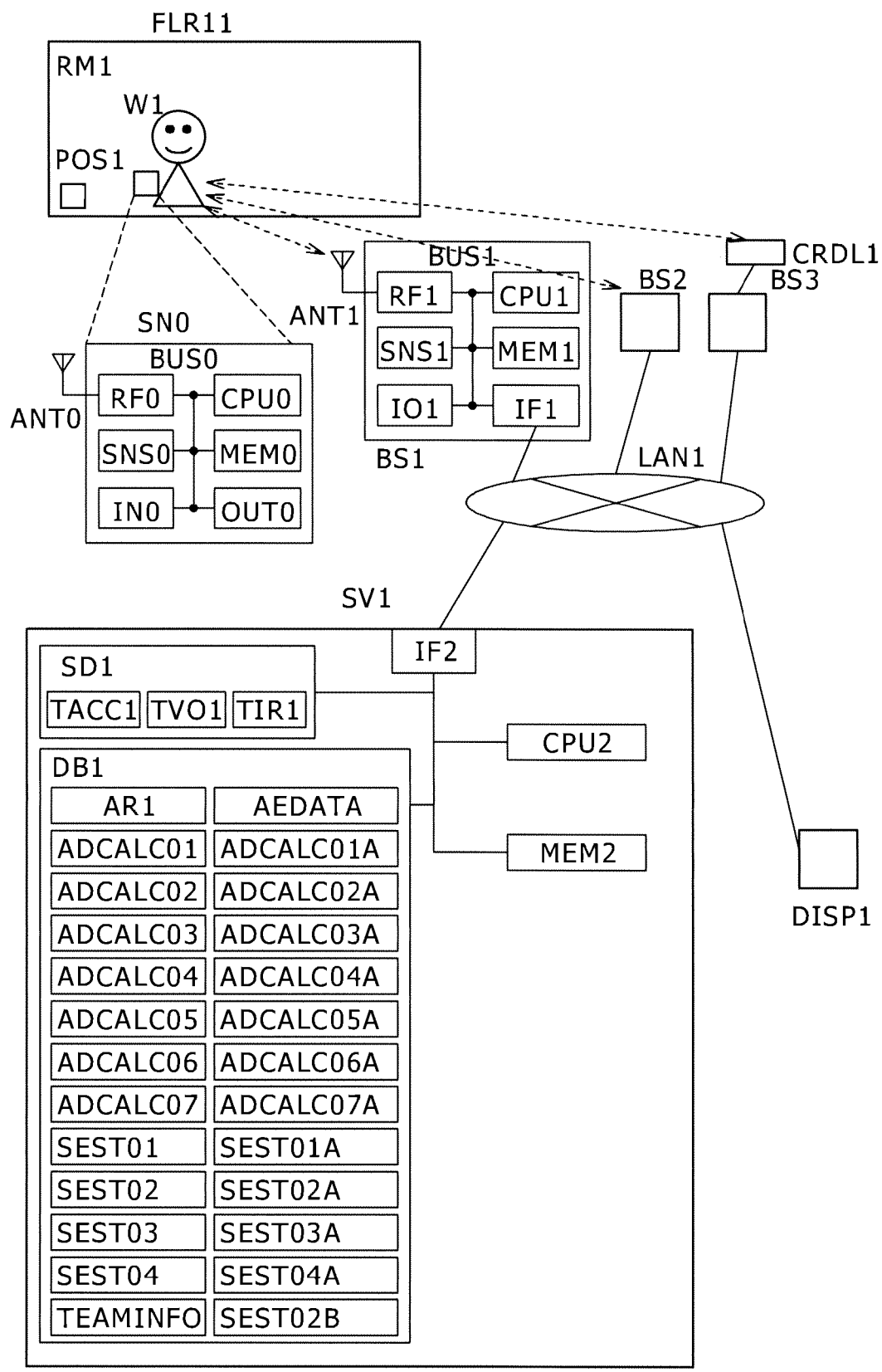
FIG. 23 is an example of the general configuration of a system for performing stress estimation by calculating the feature of the degree of continuity of action.

FIG. 23 is a view of the configuration of the system. In the present embodiment, the sensor SN0 includes at least an acceleration sensor and an infrared sensor for detecting face-to-face contact state. Further, the sensor node SN0 includes an infrared output part. Other configurations are the same as the first embodiment.

Figure 24:
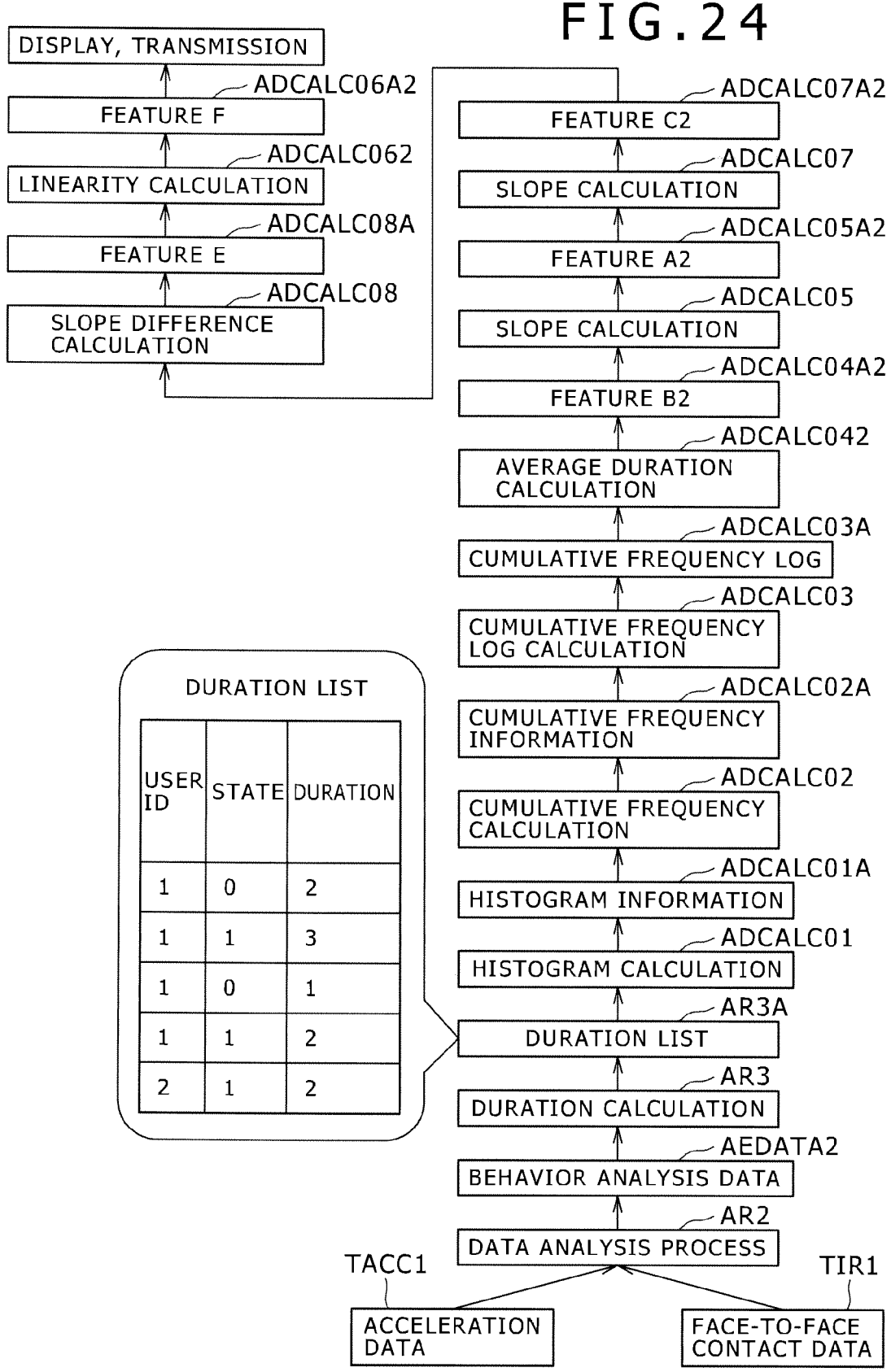
FIG. 24 is an example of the flow for calculating the feature of the degree of continuity of action.

FIG. 24 shows the entire flow of the process on the server. The server SV1 performs the process at regular intervals per day and the like, or upon request of the user if needed. Each process described below is performed by the CPU2.

Figure 25:
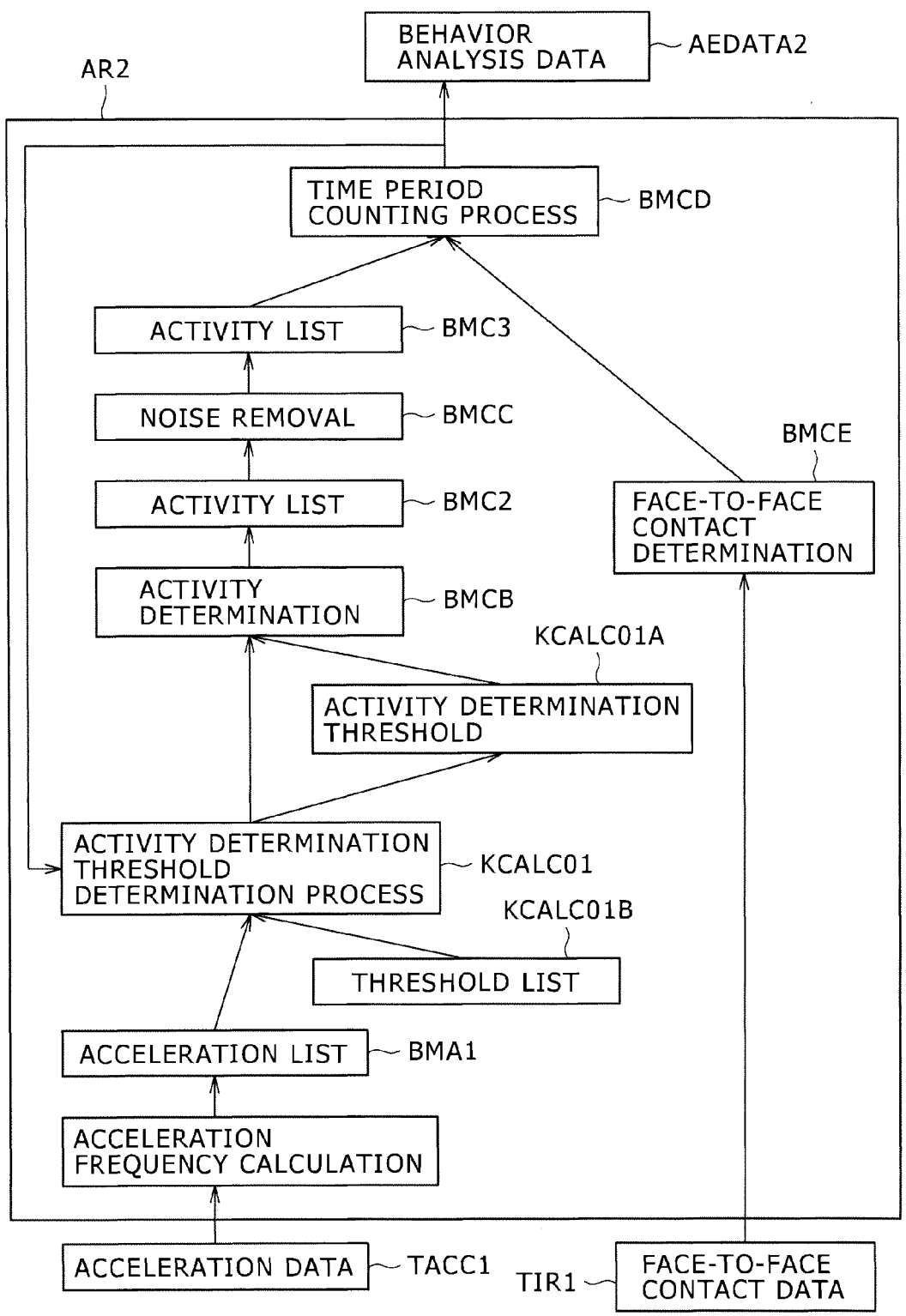
FIG. 25 is an example of the flow for calculating behavior analysis data.

First, the CPU2 performs a data analysis process AR2 from the sensor data, and calculates a behavior analysis data AEDATA2 per minute. A detailed example is shown in FIG. 25.

The CPU2 first performs AR1 (FIG. 6) by calculating the zero crossing number in each time (unit time), and storing the result in the recording device DB1. Note that the CPU2 may perform only the acceleration frequency calculation BMAA here.

Next, in an activity threshold determination process KCALC01, the CPU2 obtains one threshold for determination from a threshold list KCALC01B, and stores the determination threshold in KCALC01A. This is the process necessary to adopt standards with the highest estimated stress value, by sequentially selecting from a plurality of standards for the determination of active or inactive state, and by calculating the feature of the duration for all the selected standards. The determination threshold can be set and stored in the threshold list in advance.

Next, similar to the method described above, the CPU2 performs the activity determination BMCB, noise removal BMCC, and time period counting process BMCD to determine active or inactive state in each time. However, these processes are performed for all candidates contained in the threshold list KCALC01B and all results are stored in AEDATA2.

Next, similar to the method described above, in the face-to-face contact determination BMCE, the CPU2 identifies the activity in each time. More specifically, the CPU2 distinguishes between communication activity and individual activity.

Returning to FIG. 24, next in a duration calculation process AR3, the CPU2 calculates the duration of the active state as well as the duration of the inactive state, and stores the result in a duration list AR3A. In AR3, the CPU2 counts how long the active and inactive states continue by operating the data in chronological order with respect to the behavior analysis data AEDATA2. For example, it is assumed that the active state of a certain worker is 0, 0, 1, 1, 1, 0, 1, 1 in chronological order, where the active state is 1 and the inactive state is 0. In this case, the CPU2 calculates the duration of the period for which the same state continues with 0 or 1. More specifically, it is determined that the inactive duration is 2 minutes, the active duration is 3 minutes, the inactive duration is 1 minute, and the active duration is 2 minutes.

Next, in a histogram calculation ADCALC01, the CPU2 counts the durations obtained as describe above to generate histogram information. The following process may be the same as the process described with reference to FIG. 14. The CPU2 can calculate the features A to D for the distribution of the duration. After that, the CPU2 can perform stress estimation as shown in FIGS. 19 and 20, and display the results as shown in FIG. 21. Note that FIG. 24 is an example of obtaining features A2, B2, C2, E, and F, which will be described below, instead of the features A to D.

Figure 26:
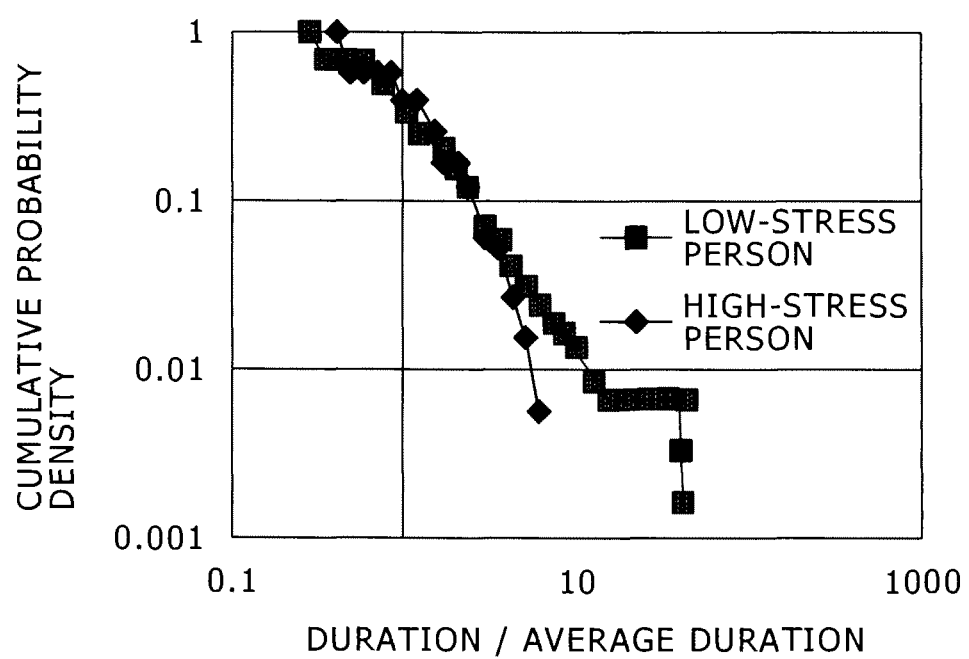
FIG. 26 is an example of the cumulative distribution of the degree of continuity of action for a worker with high stress and a worker with low stress.

FIG. 26 is an example of performing stress estimation by using the continuity features. The stress estimation was performed for 510 workers in 9 companies in total, by measuring behavior data through the name-tag type sensors and by obtaining subjective stress values through the CES-D questionnaire. The CPU2 calculates features by the procedure shown in FIG. 24. However, the CPU2 obtains the features of the distribution by another method described in FIG. 14, instead of obtaining features A to D. First, the CPU2 simply obtains the average of the duration, instead of the feature B showing the inflection point, and defines the value as feature B2 (ADCALC042). Then, the CPU2 defines the slope of the part below the feature B2 as feature A2, and the slope of the part above than B2 as feature C2 (ADCALC05, ADCALC07). Further, as another index indicating the degree of inflection, the CPU2 calculates the difference between A2 and C2 as feature E, as well as the linearity of the entire distribution as feature F (ADCALC08, ADCALC062). The feature F is similar to the features A and C. In other words, it is possible to calculate the correlation coefficient with the line, and consider the correlation coefficient as the linearity. The CPU2 calculates the 5 features for the distribution of the duration of the active state and for the distribution of the duration of the inactive state, respectively. The active and inactive states are determined using five types of thresholds, 0 Hz, 0.25 Hz, 0.6 Hz, 1 Hz, and 2 Hz. Further, three types of activities, personal work state, face-to-face contact state, and state without distinction between the two, are used. As a result, 150 indices are calculated from 2*5*5*3. A multiple regression analysis is performed using the 150 indices as explanatory variables, and using the stress values obtained through questionnaire as objective variables.

The indices with low contribution are sequentially deleted, and finally the following three indices remain as the indices with high contribution (the value t is 1 or more). The first is a feature V involved in the distribution of the active duration of more than 0.25 Hz, without distinction between the face-to-face contact state and the personal work state. It means that the activity is less likely to continue for a long time for a person with high stress. The second is a feature W involved in the distribution of the active duration of 0.25 Hz or more. The slope changes sharply for the person with high stress. In other words, it also means that the activity is less likely to continue for a long time. Further, the third is a feature X involved in the distribution of the active duration of more than 0 Hz for the personal work. The linearity is low for the person with high stress. In general, similar to the former two features, it means that the activity is less likely to continue for a long time. The three indices are common in the point that the person with high stress does not remain in the active state for a long time. Further, when only the personal work is to be analyzed as the second and third features, the relationship between activity and stress is visible, showing effectiveness in distinguishing between the personal work state and the face-to-face contact state as in the present invention. The figure shows a sample of persons with high stress and low stress. It can be found that the person with low stress has a long duration and the linearity of the distribution is high. On the other hand, the person with high stress has a small amount of long duration and the slope is steep in the range of the long duration.

Further, the stress value is estimated by using the method shown in FIGS. 19 and 20. However, as described above, the features A2, B2, C2, E, and F are used instead of the features A to D. Here, the estimation result is verified by an approach described below. First, CES-D questionnaire was conducted for a total of 510 individuals. Then, those with 16 or more are defined as high-stress group, and others are defined as low-stress group. Further, the 510 individuals are divided into two groups at random. The process in FIG. 19 is performed for one group of 205 individuals, and the feature weight is calculated by the feature weight calculation SEST03. In this embodiment, the estimated value ESTi of the stress of a certain user can be calculated from the features A2, B2, C3, E, F, and from the weights for each of the features. Here, each weight is calculated. The stress value for 205 individuals of the other group is estimated the result of the feature weight calculation. Based on the estimated stress value, those with 16 or more are considered to be high-stress individuals, and others are considered to be low-stress individuals. One of the verification standards is whether the person determined as a high-stress individual by the CES-D questionnaire, is also determined as highly stressed by the estimated value. This is called the true positive rate. As a result of the calculation, 95 individuals, or 83% of 114 individuals determined as highly stressed by the CES-D questionnaire, are also determined as highly stressed. On the other hand, 26 individuals, or only about 29% of 91 low-stress individuals are correctly estimated as low-stress individuals. The accuracy is not satisfactory yet, but can be used as a guide.

3. Configuration Example

Configuration Example 1

There is provided an information processing system including a sensor, a base station, and a server. The sensor obtains acceleration data and transmits the data to the server through the base station. The server obtains and records the number of zero crossings from the acceleration data. The server obtains and records the frequency distribution of the number of zero crossings. The server obtains and records one or more of the following: the slope of the approximate line of the distribution, the linearity of the distribution, the inflection point, the slope of the approximate line in the zero crossing range below the inflection point, the slope of the approximate line in the zero crossing range above the inflection point, the linearity of the distribution in the zero crossing range below the inflection point, and the linearity of the distribution in the zero crossing range above the inflection point. Then, the server outputs the obtained value to a display device connected to the information system.

Configuration Example 2

The information processing system of the configuration example 1 includes a questionnaire interface for asking questions about human stress. The server calculates and records the weight of each feature so that the error between the feature and the questionnaire result is reduced. The server estimates and records stress from the features and the weights of the individual features. Then, the server outputs the obtained value to a display device connected to the information system.

Configuration Example 3

There is provided an information processing system including a sensor, a base station, and a server. The sensor has a function for obtaining acceleration data, obtaining face-to-face contact data by infrared light, and transmitting the data to the server through the base station. The server obtains and records the number of zero crossings from the acceleration data. The server has information on the threshold of the number of zero crossings. The server determines whether a wearer is in the active or inactive state in each unit time, based on the number of zero crossings and on the threshold, and stores the result. The server determines whether the wearer is in the face-to-face contact state or in the personal work state in each unit time, based on the infrared information, and stores the result. The server calculates the duration of the period for which the same state continues, based on the activity determination result and the state determination result, and stores the calculation result. The server obtains and records the frequency distribution of the duration. The server calculates and stores one or more of the following: the slope of the approximate line of the distribution; the linearity of the distribution; the average duration; the slope of the approximate line of the distribution in the range of the duration shorter than the average duration; the linearity of the distribution; the slope of the approximate line of the distribution in the range of the duration longer than the average duration; the linearity of the distribution; and the difference between the slope of the approximate line of the distribution in the range of the duration shorter than the average duration, and the slope of the approximate line of the distribution in the range of the duration longer than the average duration. Then, the server outputs the value to a display device connected to the information system.

Configuration Example 4

The information processing system of the configuration example 3 includes a questionnaire interface for asking questions about human stress. The server calculates and records the weight of each feature so that the error between the feature and the questionnaire result is small. The server estimates and records stress from the features and the weights of the individual features. Then, the server outputs the value to a display device connected to the information system.

The present invention can be applied, for example, to a system that collects and stores information on the features of human movement by a sensor device.

What is claimed is:

1. An information processing system comprising:
a sensor for measuring a human acceleration produced by human movement for a predetermined time period;
a processing part for obtaining feature data related to a speed of human movement based on the measured acceleration data; and
a storage part for storing the obtained feature data,
wherein the processing part is configured to:
obtain the speed of movement per predetermined unit time from the acceleration data measured by the sensor;
count the speed of movement above a reference value, from the obtained speed of movement per unit time, with respect to each of a plurality of reference values of the speed of movement, as a cumulative frequency for the reference value of the speed of movement; and
obtain statistical data based on the distribution between the reference values of the speed of movement, and the log of the cumulative frequency for the reference values, as the feature data of human movement, and storing the feature data in the storage part,
wherein the speed of movement is a zero crossing number indicating the number of times the acceleration data is zero or crosses zero,
wherein the processing part is configured to:
obtain the number of zero crossings per predetermined unit time, as the speed of movement, from the acceleration data measured by the sensor;
count the number of zero crossings above a reference value, from the number of zero crossings obtained per unit time, with respect to each of a plurality of reference values of the zero crossing number, as a cumulative frequency for the reference value of the zero crossing number;
obtain statistical data based on the reference value of the zero crossing number and on the log of the cumulative frequency for the reference value, as feature data of human behavior; and
store the obtained feature data in the storage part.

2. An information processing system according to claim 1, wherein the processing part obtains an index indicating the slope or linearity of one approximate line or a plurality of approximate lines, as the feature data.

3. An information processing system according to claim 1, wherein the processing part obtains feature data including one or more of the following:
first feature data which is an inflection point at which the distribution between the reference value of the zero crossing number, and the log of the cumulative frequency for the reference value is approximated by a curve or a plurality of straight lines;

second feature data which is the slope of a first approximate line in the zero crossing range below the inflection point;

third feature data which is the slope of a second approximate line in the zero crossing range above the inflection point; and fourth feature data which is an index indicating the linearity of the distribution in the zero crossing range below the inflection point, wherein the processing part stores the obtained feature data in the storage part.

4. An information processing system according to claim 3, wherein the feature data includes all of the first to fourth feature data.

5. An information processing system according to claim 3, wherein the feature data further includes one or more of the following:
the slope of the approximate line of the entire distribution;
the linearity of the entire distribution; and
the linearity of the distribution in the zero crossing range above the inflection point.

6. An information processing system according to claim 3 comprising a plurality of sensors,
wherein the plurality of sensors measure the acceleration of each person to be measured,
wherein the processing part is configured to:
obtain the first to fourth feature data for each person to be measured;
input the previously indexed stress value of the person to be measured;
obtain each weight coefficient so that the sum of the error between the estimated stress value obtained based on the obtained first to fourth feature data and on the weight coefficients of each of the first to fourth feature data, and the input stress value is reduced, with respect to each person to be measured; and
store the obtained weight coefficient in the storage part.

7. An information processing system according to claim 6, wherein the processing part obtains the estimated stress value based on the obtained first to fourth feature data and on the weight coefficients for each of the first to fourth feature data, and stores the estimated stress value in the storage part.

8. An information processing system according to claim 1, wherein the processing part obtains feature data including one or more of the following:
the average of the number of zero crossings;
the slope of a third approximate line in the zero crossing range below the average of the number of zero crossings;
the slope of a fourth approximate line in the zero crossing range above the average of the number of zero crossings;
the difference between the slope of the third approximate line and the slope of the fourth approximate line; and
the slope of the approximate line of the entire distribution.

9. An information processing system according to claim 1, wherein the processing part outputs the obtained feature data to a display device.

10. An information processing system according to claim 1, comprising:
a sensor node including the sensor and a transmission part for transmitting measured acceleration data; and
a server including a receiving part for receiving the acceleration data from the sensor node, the processing part, and the storage part.

11. An information processing system according to claim 1 comprising a sensor node including the sensor, the processing part, and the storage part.

12. An information processing system comprising:
a sensor for measuring a human acceleration produced by human movement for a predetermined time period;
a processing part for obtaining feature data of a speed of human movement based on the measured acceleration data; and
a storage part for storing the obtained feature data,
wherein the processing part is configured to:
obtain the speed of movement per predetermined unit time from the acceleration data measured by the sensor;
determine active or inactive state in each time period, based on whether the speed of movement per unit time exceeds a predetermined threshold;
obtain the duration of the active state and/or the duration of the inactive state in a chronological order;
count the duration above a reference value, from the obtained duration of the active state and/or the obtained duration of the inactive state, with respect to each of a plurality of reference values of the duration, as a cumulative frequency for the reference value of the duration;
obtaining statistical data based on the distribution between the reference value of the duration and on the log of the cumulative frequency for the reference value, as the feature data of human behavior; and
store the obtained feature data in the storage part,
wherein the processing part obtains feature data including one or more of the following:
first feature data which is the inflection point at which the distribution between the reference value of the duration, and the log of the cumulative frequency for the reference value, is approximated by a curve or a plurality of straight lines;
second feature data which is slope a first approximate line in the duration range below the inflection point;
third feature data which is the slope of a second approximate line in the duration range above the inflection point;
fourth feature data which is an index indicating the linearity of the distribution in the duration range below the inflection point;
fifth feature data which is the average of the duration;
sixth feature data which is the slope of a third approximate line in the duration range below the average of the duration; and
seventh feature data which is the slope of a fourth approximate line in the duration range above the average of the duration,
wherein the processing part stores the obtained feature data in the storage part.

13. An information processing system according to claim 12,
wherein the speed of movement is the zero crossing number indicating the number of times the acceleration data is zero or crosses zero.

14. An information processing system according to claim 12,
wherein the processing part obtains an index indicating the slope or linearity of one approximate line or a plurality of approximate lines for the distribution, as the feature data.

15. An information processing system according to claim 12,
wherein the feature data further includes one or more of the following:
the difference between the slope of the third approximate line and the slope of the fourth approximate line; and
the index indicating the linearity of the entire distribution.

16. An information processing method comprising:
obtaining, by a processing part, a speed of movement per predetermined unit time, from acceleration data measured by a sensor for measuring a human acceleration produced by a human movement for a predetermined time period;
counting, by the processing part, the speed of movement above a reference value, from the obtained speed of movement per unit time, with respect to each of a plurality of reference values of the speed of movement, as a cumulative frequency for the reference value of the speed of movement;
obtaining, by the processing part, statistical data based on the distribution between the reference value of the speed of movement and the log of the cumulative frequency for the reference value, as feature data of human behavior, and storing the obtained feature data in a storage unit,
wherein the speed of movement is a zero crossing number indicating the number of times the acceleration data is zero or crosses zero,
wherein the method further comprising:
obtaining, by the processing part, the number of zero crossings per predetermined unit time, as the speed of movement, from the acceleration data measured by the sensor;
counting, by the processing part, the number of zero crossings above a reference value, from the number of zero crossings obtained per unit time, with respect to each of a plurality of reference values of the zero crossing number, as a cumulative frequency for the reference value of the zero crossing number;
obtaining, by the processing part, statistical data based on the reference value of the zero crossing number and on the log of the cumulative frequency for the reference value, as the feature data of human behavior; and
storing, by the processing part, the obtained feature data in the storage unit.

17. An information processing method comprising:
obtaining, by a processing unit, a speed of movement per predetermined unit time, from acceleration data measured by a sensor for measuring a human acceleration produced by human movement for a predetermined time period;
determining, by the processing part, active or inactive state in a particular time, based on whether the speed of movement per unit time exceeds a predetermined threshold;
obtaining, by the processing part, the duration of the active state and/or the duration of the inactive state in a chronological order;
counting, by the processing part, the duration above a reference value, from the obtained duration of the active state and/or the obtained duration of the inactive state, with respect to each of a plurality of reference values of the duration, as a cumulative frequency for the reference value of the duration; and
obtaining, by the processing part, statistical data based on the distribution between the reference value of the duration and the log of the cumulative frequency for the reference value, as feature data of human behavior, and storing the obtained feature data in a storage unit,
wherein the speed of movement is a zero crossing number indicating the number of times the acceleration data is zero or crosses zero,
wherein the method further comprises:
obtaining, by the processing part, the number of zero crossings per predetermined unit time, as the speed of movement, from the acceleration data measured by the sensor;
counting, by the processing part, the number of zero crossings above a reference value, from the number of zero crossings obtained per unit time, with respect to each of a plurality of reference values of the zero crossing number, as a cumulative frequency for the reference value of the zero crossing number;
obtaining, by the processing part, statistical data based on the reference value of the zero crossing number and on the log of the cumulative frequency for the reference value, as the feature data of human behavior; and
storing, by the processing part, the obtained feature data in the storage unit.

* * * * *